US 6,524,257 B2

(12) United States Patent
Ogura

(10) Patent No.: US 6,524,257 B2
(45) Date of Patent: Feb. 25, 2003

(54) SUPERIOR-AND-INFERIOR-LIMB BLOOD-PRESSURE INDEX MEASURING APPARATUS

(75) Inventor: Toshihiko Ogura, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/977,332

(22) Filed: Oct. 16, 2001

(65) Prior Publication Data

US 2002/0133082 A1 Sep. 19, 2002

(30) Foreign Application Priority Data

Mar. 15, 2001 (JP) ........................................ 2001-073940

(51) Int. Cl.⁷ ................................................ A61B 5/00
(52) U.S. Cl. ........................ 600/490; 600/494; 600/495
(58) Field of Search .............................. 600/490, 493–6

(56) References Cited

U.S. PATENT DOCUMENTS 5,241,963 A     9/1993    Shankar
6,379,309 B1 * 4/2002 Ogura et al. ................ 600/490

FOREIGN PATENT DOCUMENTS

EP     1 050 267 A1     11/2000

EP     1 053 714 A2     11/2000

* cited by examiner

*Primary Examiner*—Robert L. Nasser
(74) *Attorney, Agent, or Firm*—Oliff & Berridge PLC

(57) ABSTRACT

An apparatus for measuring a superior-and-inferior-limb blood-pressure index of a living subject, including an inferior-limb-blood-pressure measuring device which includes an inferior-limb cuff adapted to be wound around an inferior limb of the subject and which measures an inferior-limb blood pressure of the inferior limb, a superior-limb-blood-pressure measuring device which includes a superior-limb cuff adapted to be wound around a superior limb of the subject and which measures a superior-limb blood pressure of the superior limb, a blood-pressure-index determining device for determining the superior-and-inferior-limb blood-pressure index, based on the inferior-limb blood pressure measured by the inferior-limb-blood-pressure measuring device and the superior-limb blood pressure measured by the superior-limb-blood-pressure measuring device, an inferior-limb-pulse-wave detecting device which is adapted to be worn on an inferior limb of the subject and which detects an inferior-limb pulse wave from the inferior limb, and a stenosis-relating-pulse-wave-information obtaining device which obtains, based on the inferior-limb pulse wave detected by the inferior-limb-pulse-wave detecting device, stenosis-relating pulse-wave information which changes in relation with a degree of stenosis of an artery of the inferior limb.

9 Claims, 8 Drawing Sheets

SUPERIOR-AND-INFERIOR-LIMB BLOOD-PRESSURE INDEX MEASURING APPARATUS

BACKGROUND OF THE INVENTION

1. Field of the Invention

The present invention relates to an apparatus for measuring a superior-and-inferior-limb blood-pressure index of a living subject.

2. Related Art Statement

A blood pressure of an inferior limb (hereinafter, referred to as "inferior-limb blood pressure") of a normal person is higher than a blood pressure of a superior limb (hereinafter, referred to as "superior-limb blood pressure") of the person. However, if arteries of the inferior limb of the person suffer stenosis, the inferior-limb blood pressure may be lower than the superior-limb blood pressure. This can be utilized to diagnose the stenosis of arteries of inferior limb. For example, European Patent Document No. 1053714 A2 discloses a superior-and-inferior-limb blood-pressure index measuring apparatus which determines a superior-and-inferior-limb blood-pressure index as a ratio of an inferior-limb blood pressure to a superior-limb blood pressure or a ratio of a superior-limb blood pressure to an inferior-limb blood pressure.

The determination of superior-and-inferior-limb blood-pressure index needs measurements of inferior-limb blood pressure and superior-limb blood pressure. To this end, generally, those blood-pressure measuring devices are used which include respective inflatable cuffs adapted to be wound around an inferior limb and a superior limb of a living subject and each of which determines a blood pressure based on a signal occurring to a corresponding one of the cuffs when a pressure in the cuff is slowly changed. The blood-pressure measuring devices utilizing the cuffs provide highly reliable blood-pressure values. Since a superior-and-inferior-limb blood-pressure index determined based on inferior-limb and superior-limb blood-pressure values measured using cuffs is highly reliable, the diagnosis of stenosis of arteries of inferior limb can be made with accuracy.

However, when a blood-pressure measuring device utilizing an inflatable cuff is used to measure a blood pressure of a patient, it is needed to increase a pressure in the cuff up to a prescribed target pressure higher than a systolic blood pressure of the patient. In addition, since an inferior-limb blood pressure of a normal person is higher than a superior-limb blood pressure of the person, it is needed, when the inferior-limb blood pressure is measured, to increase the pressure of the cuff up to a higher target pressure than the target pressure employed for the measurement of superior-limb blood pressure. For example, a target pressure employed by a superior-limb-blood-pressure measuring device is about 180 mmHg, whereas a target pressure employed by an inferior-limb-blood-pressure measuring device is about 240 mmHg. Thus, when an inferior-limb blood pressure is measured from a patient, the patient feels more discomfort than when a superior-limb blood pressure is measured from the same.

SUMMARY OF THE INVENTION

It is therefore an object of the present invention to provide a superior-and-inferior-limb blood-pressure index measuring apparatus which allows diagnosis of stenosis of inferior-limb artery of a patient, without causing the patient to feel much discomfort.

The Inventor has carried out extensive studies and found that information obtained from an inferior-limb pulse wave contains information (hereinafter, referred to as "stenosis-relating pulse-wave information") that changes in relation with a degree of stenosis of inferior-limb artery. If a superior-and-inferior-limb blood-pressure index is measured only when a preliminary judgment made about the stenosis of inferior-limb artery based on the stenosis-relating pulse-wave information indicates that the inferior-limb artery is suspected of the stenosis, diagnosis of stenosis of inferior-limb artery of a patient can be made without causing the patient to feel much discomfort. The present invention has been developed based on this finding.

The above object has been achieved by the present invention. According to the present invention, there is provided an apparatus for measuring a superior-and-inferior-limb blood-pressure index of a living subject, comprising an apparatus for measuring a superior-and-inferior-limb blood-pressure index of a living subject, comprising an inferior-limb-blood-pressure measuring device which includes at least one inferior-limb cuff adapted to be wound around at least one inferior limb of the subject and which measures at least one inferior-limb blood pressure of the inferior limb; a superior-limb-blood-pressure measuring device which includes at least one superior-limb cuff adapted to be wound around at least one superior limb of the subject and which measures at least one superior-limb blood pressure of the superior limb; a blood-pressure-index determining means for determining the superior-and-inferior-limb blood-pressure index, based on the inferior-limb blood pressure measured by the inferior-limb-blood-pressure measuring device and the superior-limb blood pressure measured by the superior-limb-blood-pressure measuring device; an inferior-limb-pulse-wave detecting device which is adapted to be worn on an inferior limb of the subject and which detects an inferior-limb pulse wave from the inferior limb; and a stenosis-relating-pulse-wave-information obtaining device which obtains, based on the inferior-limb pulse wave detected by the inferior-limb-pulse-wave detecting device, stenosis-relating pulse-wave information which changes in relation with a degree of stenosis of an artery of the inferior limb.

According to this invention, before the inferior-limb-blood-pressure measuring device measures the inferior-limb blood pressure, the stenosis-relating-pulse-wave-information obtaining device may obtain, from the inferior-limb pulse wave detected by the inferior-limb-pulse-wave detecting device, the stenosis-relating pulse-wave information. If the thus obtained stenosis-relating pulse-wave information indicates that the artery of the inferior limb is not suspected of the stenosis, the inferior-limb-blood-pressure measuring device need not measure the inferior-limb blood pressure to determine the superior-and-inferior-limb blood-pressure index. Therefore, the diagnosis of stenosis of inferior-limb artery can be made without causing the subject to feel much discomfort. This diagnosis may be made either automatically by the apparatus, or by a living person.

Preferably, the apparatus further comprises a preliminary-judgment making means for making a preliminary judgment that the artery of the inferior limb is suspected of the stenosis, when the stenosis-relating pulse-wave information obtained by the stenosis-relating-pulse-wave-information obtaining device falls in a predetermined abnormal range; and a blood-pressure-measurement starting means for, when the preliminary-judgment making means makes the preliminary judgment that the artery of the inferior limb is suspected of the stenosis, starting the inferior-limb-bloodpressure measuring device to measure the inferior-limb blood pressure of the inferior limb, and starting the superior-limb-blood-pressure measuring device to measure the superior-limb blood pressure of the superior limb, so that the blood-pressure-index determining means determines the superior-and-inferior-limb blood-pressure index, based on the inferior-limb blood pressure measured by the inferior-limb-blood-pressure measuring device and the superior-limb blood pressure measured by the superior-limb-blood-pressure measuring device.

According to this feature, when the preliminary-judgment making means makes the preliminary judgment that the artery of the inferior limb is suspected of the stenosis, the blood-pressure-measurement starting means automatically starts the inferior-limb-blood-pressure measuring device to measure the inferior-limb blood pressure of the inferior limb, and starts the superior-limb-blood-pressure measuring device to measure the superior-limb blood pressure of the superior limb, and finally the blood-pressure-index determining means automatically determines the superior-and-inferior-limb blood-pressure index, based on the thus measured inferior-limb blood pressure and the thus measured superior-limb blood pressure.

Preferably, the stenosis-relating-pulse-wave-information obtaining device comprises at least one of (a) an inferior-limb-pulse-wave-propagation-velocity-relating-information obtaining device which obtains, based on the inferior-limb pulse wave detected by the inferior-limb-pulse-wave detecting device, inferior-limb -pulse-wave-propagation-velocity-relating information relating to a velocity at which the inferior-limb pulse wave propagates through the artery of the inferior limb, (b) a sharpness-degree determining means for determining a degree of sharpness of a heartbeat-synchronous pulse of the inferior-limb pulse wave detected by the inferior-limb-pulse-wave detecting device; and (c) an increase-characteristic-value determining means for determining a characteristic value of an increasing portion of a heartbeat-synchronous pulse of the inferior-limb pulse wave detected by the inferior-limb-pulse-wave detecting device.

Preferably, the stenosis-relating-pulse-wave-information obtaining device comprises an inferior-limb-pulse-wave-propagation-velocity-relating-information obtaining device which obtains, based on the inferior-limb pulse wave detected by the inferior-limb-pulse-wave detecting device, inferior-limb-pulse-wave-propagation-velocity-relating information relating to a velocity at which the inferior-limb pulse wave propagates through the artery of the inferior limb, and the apparatus further comprises a superior-limb-pulse-wave detecting device which is adapted to be worn on a superior limb of the subject and which detects a superior-limb pulse wave from the superior limb; a superior-limb-pulse-wave-propagation-velocity-relating-information obtaining device which obtains, based on the superior-limb pulse wave detected by the superior-limb-pulse-wave detecting device, superior-limb-pulse-wave-propagation-velocity-relating information relating to a velocity at which the superior-limb pulse wave propagates through an artery of the superior limb; a normal-range determining means for determining, based on the superior-limb-pulse-wave-propagation-velocity-relating information obtained by the superior-limb -pulse-wave-propagation-velocity-relating-information obtaining device, a normal range of inferior-limb-pulse-wave-propagation-velocity-relating information, according to a predetermined relationship between inferior-limb-pulse-wave-propagation-velocity-relating information and superior-limb-pulse-wave-propagation-velocity-relating information; and a preliminary-judgment making means for making a preliminary judgment that the artery of the inferior limb is suspected of the stenosis, when the inferior-limb-pulse-wave-propagation-velocity-relating information obtained by the inferior-limb-pulse-wave-propagation-velocity-relating-information obtaining device does not fall in the normal range determined by the normal range determining means.

According to this feature, the normal-range determining means determines, based on the superior-limb-pulse-wave-propagation-velocity-relating information, the normal range of inferior-limb-pulse-wave-propagation-velocity-relating information, according to the predetermined relationship, and the preliminary-judgment making means makes the preliminary judgment that the artery of the inferior limb is suspected of the stenosis, when the inferior-limb-pulse-wave-propagation-velocity-relating information obtained by the inferior-limb-pulse-wave-propagation-velocity-relating-information obtaining device does not fall in the thus determined normal range. Since the normal range is determined based on the superior-limb-pulse-wave-propagation-velocity-relating information actually obtained in each measuring operation, the preliminary judgment made about whether the inferior-limb artery is suspected of the stenosis is more accurate than a judgment which would be made in the case where inferior-limb-pulse-wave-propagation-velocity-relating information actually obtained is compared with a general-purpose normal range which is so predetermined as to be applicable to a great number of patients.

Preferably, the inferior-limb-pulse-wave detecting device comprises two detecting members which are adapted to be worn on a left and a right inferior limb of the subject, respectively, and which detect a left-inferior-limb pulse wave and a right-inferior-limb pulse wave from the left and right inferior limbs, respectively, and the stenosis-relating-pulse-wave-information obtaining device comprises means for obtaining, based on the detected left-inferior-limb pulse wave, left-inferior-limb-stenosis-relating pulse-wave information which changes in relation with a degree of stenosis of an artery of the left inferior limb, and means for obtaining, based on the detected right-inferior-limb pulse wave, right-inferior-limb-stenosis-relating pulse-wave information which changes in relation with a degree of stenosis of an artery of the right inferior limb.

According to this feature, if the left-inferior-limb-stenosis-relating pulse-wave information obtained based on the left-inferior-limb pulse wave is compared with the right-inferior-limb-stenosis-relating pulse-wave information obtained based on the right-inferior-limb pulse wave and it is found that a difference between the two sorts of information is significantly great, it is said that there is possibility that the great difference would result from the stenosis of artery of at least one of the left and right inferior limbs. Thus, an accurate preliminary judgment about whether the arteries of inferior limbs are suspected of stenosis can be obtained.

Preferably, the apparatus further comprises a preliminary-judgment making means for making a preliminary judgment that the artery of at least one of the left and right inferior limbs is suspected of the stenosis, when a relative value between the obtained left-inferior-limb-stenosis-relating pulse-wave information and the obtained right-inferior-limb-stenosis-relating pulse-wave information is greater than a prescribed reference value.

According to this feature, if the relative value between the left-inferior-limb-stenosis-relating pulse-wave information and the right-inferior-limb-stenosis-relating pulse-wave information is greater than the prescribed reference value, the preliminary-judgment making means makes the preliminary judgment that the artery of at least one of the left and right inferior limbs is suspected of the stenosis. Thus, an accurate preliminary judgment about whether the artery of the inferior limb is suspected of stenosis can be made.

BRIEF DESCRIPTION OF THE DRAWINGS

The above and optional objects, features, and advantages of the present invention will be better understood by reading the following detailed description of the preferred embodiments of the invention when considered in conjunction with the drawings, in which.

DETAILED DESCRIPTION OF PREFERRED EMBODIMENTS

Figure 1:
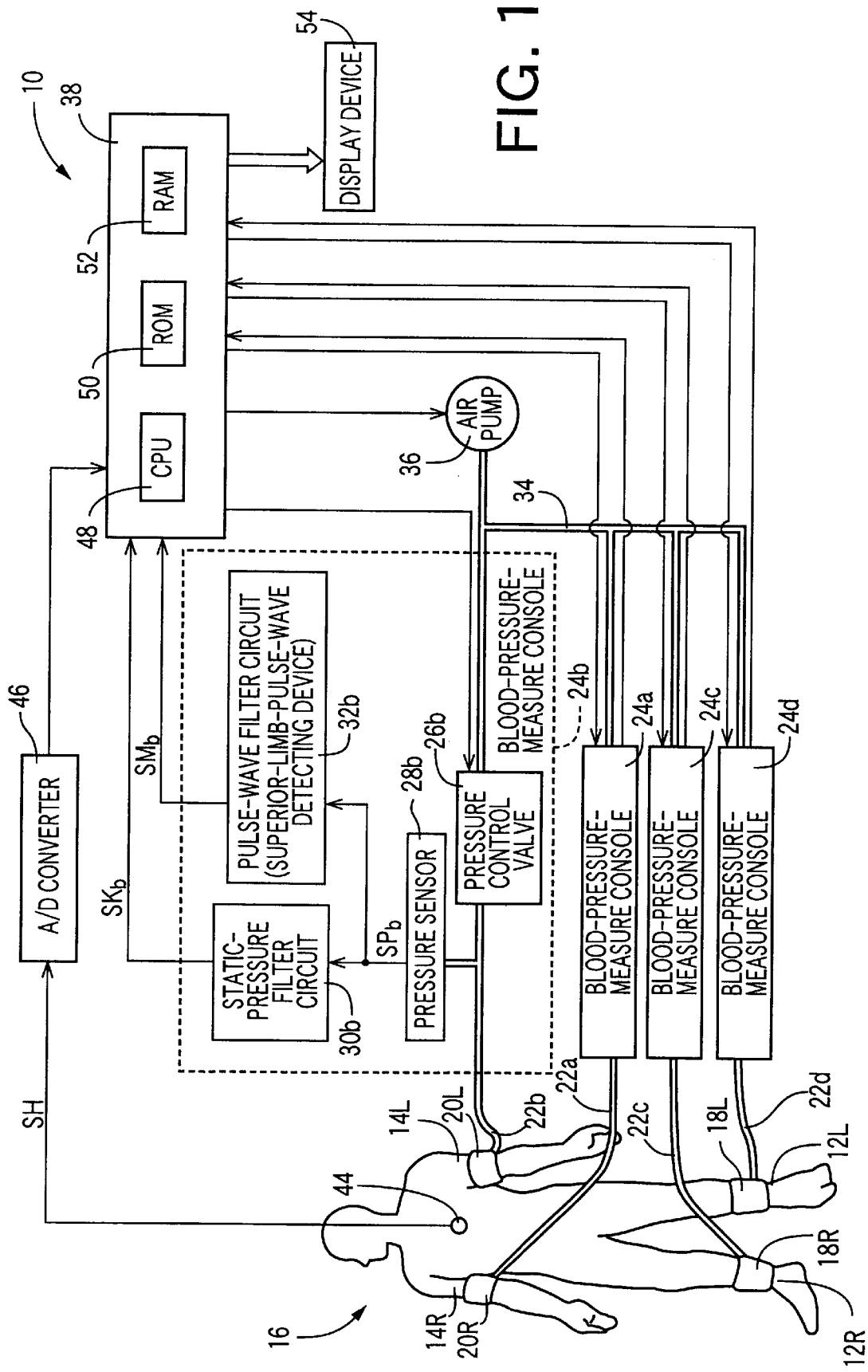
FIG. 1 is a diagrammatic view for explaining a construction of an ankle/upper-arm blood-pressure index (ABI) measuring apparatus to which the present invention is applied.

Hereinafter, there will be described an embodiment of the present invention in detail by reference to the drawings. FIG. 1 shows a diagrammatic view for explaining a construction of an ankle/upper-arm blood-pressure (BP) index measuring apparatus 10 to which the present invention is applied. The ankle/upper-arm BP index measuring apparatus 10 is a sort of superior-and-inferior-limb BP index measuring apparatus, since the apparatus 10 measures, as an inferior-limb BP value, a BP value from an ankle 12 (a right ankle 12R or a left ankle 12L) of a patient 16 as a living person and measures, as a superior-limb BP value, a BP value from an upper arm 14 (a right upper arm 14R or a left upper arm 14L) of the patient. The present apparatus 10 carries out measurements on the patient who takes a face-down, lateral, or face-up position so that the upper arms 14 and the ankles 12 are substantially level with each other.

In FIG. 1, the ankle/upper-arm BP index measuring apparatus 10 includes two ankle cuffs 18R, 18L which are wound around the two ankles 12R, 12L, respectively, and two upper-arm cuffs 20R, 20L which are wound around the two upper arms 14R, 14L, respectively. Each of the cuffs 18, 20 functions as a pressing band which presses a portion of the patient around which the each cuff is wound, and includes a belt-like outer bag which is formed of a non-stretchable material such as cloth or polyester; and a rubber bag accommodated in the outer bag.

The two upper-arm cuffs 20R, 20L are connected via respective pipings 22a, 22b to respective BP-measure consoles 24a, 24b; and the two ankle cuffs 18R, 18L are connected via respective pipings 22c, 22d to respective BP-measure consoles 24c, 24d.

Since the four BP-measure consoles 24a, 24b, 24c, 24d have an identical construction, the BP-measure console 24b to which the upper-arm cuff 20L is connected will be described below as a representative of the four devices 24a, 24b, 24c, 24d. The BP-measure console 24b includes a pressure control valve 26b, a pressure sensor 28b, a static-pressure filter circuit 30b, and a pulse-wave filter circuit 32b, and the piping 22b is connected to the pressure control valve 26b and the pressure sensor 28b. The pressure control valve 26b is connected via a piping 34 to an air pump 36.

The pressure control valve 26b is selectively placed in one of four positions, that is, a pressure-supply position in which the control valve 26b allows a pressurized air to be supplied from the air pump 36 to the upper-arm cuff 20L, a pressure-maintain position in which the control valve 26b maintains the pressure in the upper-arm cuff 20L, a slow deflation position in which a degree of opening of an electrically operated valve member of the control valve 26b is controlled to decrease, at a prescribed rate, the pressure in the upper-arm cuff 20L, and a quick-deflation position in which the control valve 26b allows the pressurized air to be quickly discharged from the upper-arm cuff 20L.

The pressure sensor 28b detects the air pressure in the upper-arm cuff 20L, and supplies a pressure signal, $SP_b$, representing the detected air pressure, to the static-pressure filter circuit 30b and the pulse-wave filter circuit 32b. The static-pressure filter circuit 30b includes a low-pass filter which extracts, from the pressure signal $SP_b$, a cuff-pressure signal, $SK_b$, representing a cuff pressure, $PC_b$, as a static component of the detected air pressure. The filter circuit 30b supplies the cuff-pressure signal $SK_b$ to a control device 38 via an analog-to-digital (A/D) converter, not shown.

The pulse-wave filter circuit 32b includes a band-pass filter which extracts, from the pressure signal $SP_b$, a pulse-wave signal, $SM_b$, representing a pulse wave $WA_L$ as an oscillatory component of the detected air pressure that has prescribed frequencies. The filter circuit 32b supplies the pulse-wave signal $SM_b$ to the control device 38 via an A/D converter, not shown. Since the pulse-wave signal $SM_b$ represents the pulse wave $WA_L$ as an oscillatory pressure wave that is produced by an artery of the left upper arm 14L pressed by the upper-arm cuff 20L, the pulse-wave filter circuit 32b functions as a superior-limb-pulse-wave detecting device. Similarly, a pulse-wave filter circuit 32a of the BP-measure console 24a functions as a superior-limb-pulse-wave detecting device which provides a pulse-wave signal $SM_a$ representing a pulse wave $WA_R$ as an oscillatory pressure wave that is produced by an artery of the right upper arm 14R pressed by the upper-arm cuff 20R; a pulse-wave filter circuit 32c of the BP-measure console 24c functions as an inferior-limb-pulse-wave detecting device which provides a pulse-wave signal $SM_c$ representing a pulse wave $WL_R$ as an oscillatory pressure wave that is produced by an artery of the right ankle 12R pressed by the ankle cuff 18R; and a pulse-wave filter circuit 32d of the BP-measure console 24d functions as an inferior-limb-pulse-wave detecting device which provides a pulse-wave signal $SM_d$ representing a pulse wave $WL_L$ as an oscillatory pressure wave that is produced by an artery of the left ankle 12L pressed by the ankle cuff 18L.

The upper-arm cuff 20L, the BP-measure console 24b, and the air pump 36 cooperate with one another to provide an upper-arm BP measuring device 40L. Similarly, the upper-ram cuff 20R, the BP-measure console 24a, and the air pump 36 cooperate with one another to provide an upper-arm BP measuring device 40R; the ankle cuff 18R, the BP-measure console 24c, and the air pump 36 cooperate with one another to provide an ankle BP measuring device 42R; and the ankle cuff 18L, the BP-measure console 24d, and the air pump 36 cooperate with one another to provide an ankle BP measuring device 42L.

A heart-sound microphone 44 is attached to a prescribed position on the skin of the chest of the patient, and detects heart sounds which are transmitted from the heart to the prescribed position on the skin. The microphone 44 converts the heart sounds detected thereby into an electric signal, i.e., a heart-sound signal, SH, and supplies the heart-sound signal SH, to the control device 38 via an A/D converter 46. Since the heart sounds represented by the heart-sound signal SH are a heartbeat-synchronous signal which is produced in synchronism with the heartbeat of the patient, the heart-sound microphone 44 functions as a heartbeat-synchronous-signal detecting device.

The control device 38 is essentially provided by a microcomputer including a central processing unit (CPU) 48, a read only memory (ROM) 50, a random access memory (RAM) 52, and an input-and-output (I/O) port, not shown, and processes signals according to the control programs pre-stored in the ROM 50, while utilizing the temporary-storage function of the RAM 52. The control device 38 outputs, from the I/O port, drive signals to the air pump 36 and the respective pressure control valves 26 (26a, 26b, 26c, 26d) of the four BP-measure consoles 24 (24a, 24b, 24c, 24d), so as to control the respective operations of those elements 36, 26 and determine an ankle/upper-arm blood-pressure index (ABI) of the patient. In addition, the control device 38 controls a display device 54 to display the thus determined index ABI.

Figure 2:
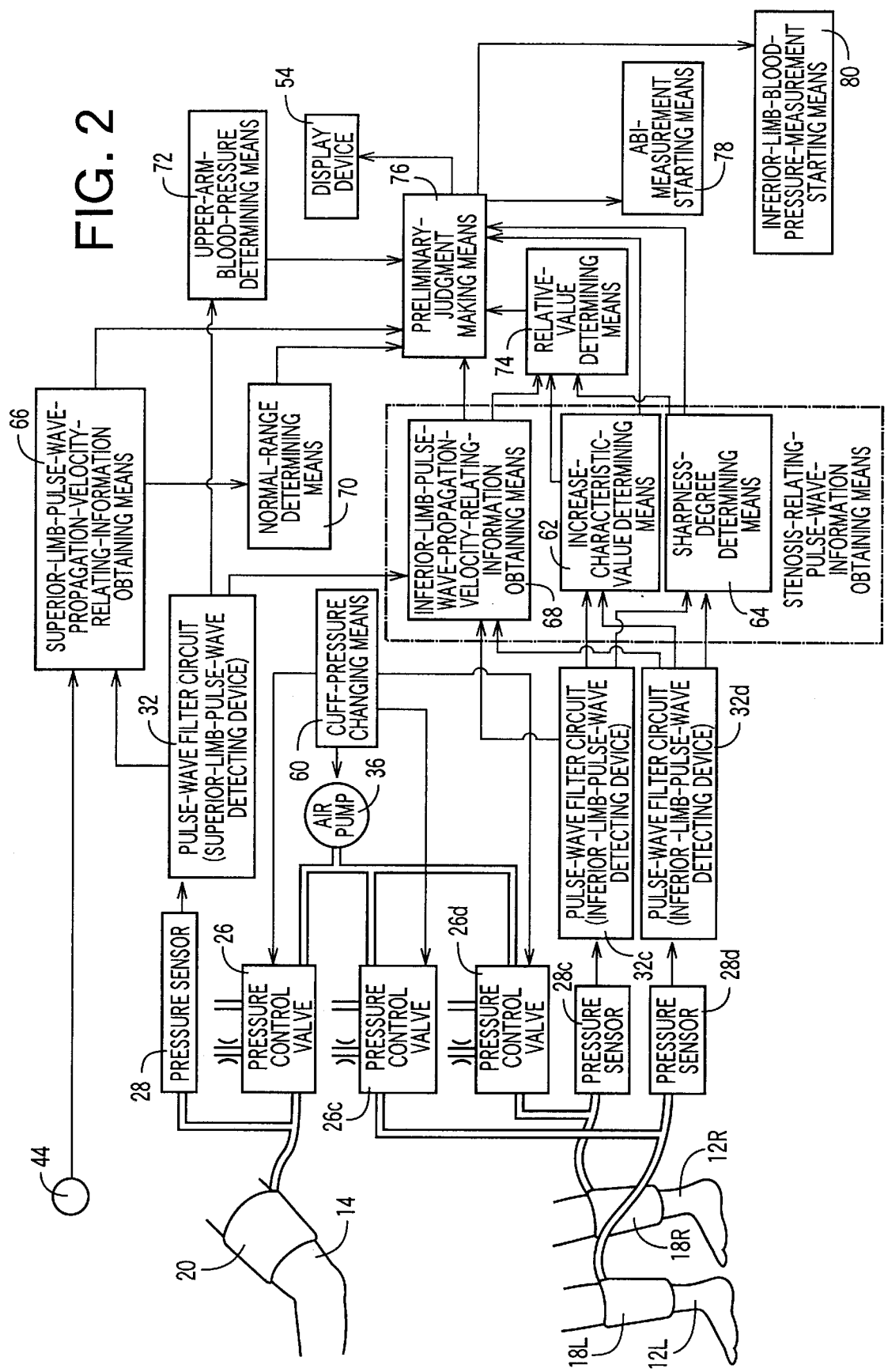
FIG. 2 is a diagrammatic view for explaining essential functions of a control device of the apparatus of FIG. 1 that relates to a preliminary judgment about whether a patient is so suspected of arteriostenosis as to need an ABI measurement.

FIG. 2 is a diagrammatic view for explaining essential control functions of the control device 38 that relate to a preliminary judgment about whether a patient is so suspected of arteriostenosis as to need an ABI measurement.

A cuff-pressure changing means 60 controls, in a blood-pressure measuring operation, the air pump 36 and the four pressure control valves 26a, 26b, 26c, 26d, such that the respective pressures $PC_a$, $PC_b$ of the two upper-arm cuffs 20R, 20L are quickly increased up to a first prescribed target pressure value $P_{CM}$ (e.g., about 180 mmHg) and the respective pressures $PC_c$, $PC_d$ of the two ankle cuffs 18R, 18L are quickly increased up to a second prescribed target pressure value $P_{CM}$ (e.g., about 240 mmHg), and then the pressures $PC_a$, $PC_b$, $PC_c$, $PC_d$ are slowly decreased at a rate of about 5 mmHg/sec. In addition, in order to obtain pieces of stenosis-relating pulse-wave information, the air pump 36 and the four pressure control valves 26a, 26b, 26c, 26d connected thereto are controlled by the changing means 60 such that the cuff pressures $PC_a$, $PC_b$, $PC_c$, $PC_d$ are increased up to a prescribed pulse-wave-detection pressure and are maintained at that pressure for a prescribed time duration. The pulse-wave-detection pressure is prescribed at a value which is lower than a common diastolic blood pressure and which assures that respective oscillatory pressure waves are produced by respective arteries under the four cuffs 18 (18R, 18L), 20 (20R, 20L), and are transmitted to the four cuffs 18, 20 so that respective pulse waves (i.e., respective pulse-wave signals $SM_a$, $SM_b$, $SM_c$, $SM_d$) representing the respective oscillatory pressure waves and each having a sufficiently great signal strength are detected from the four cuffs 18, 20. The pulse-wave-detection pressure may be 60 mmHg.

Figure 3:
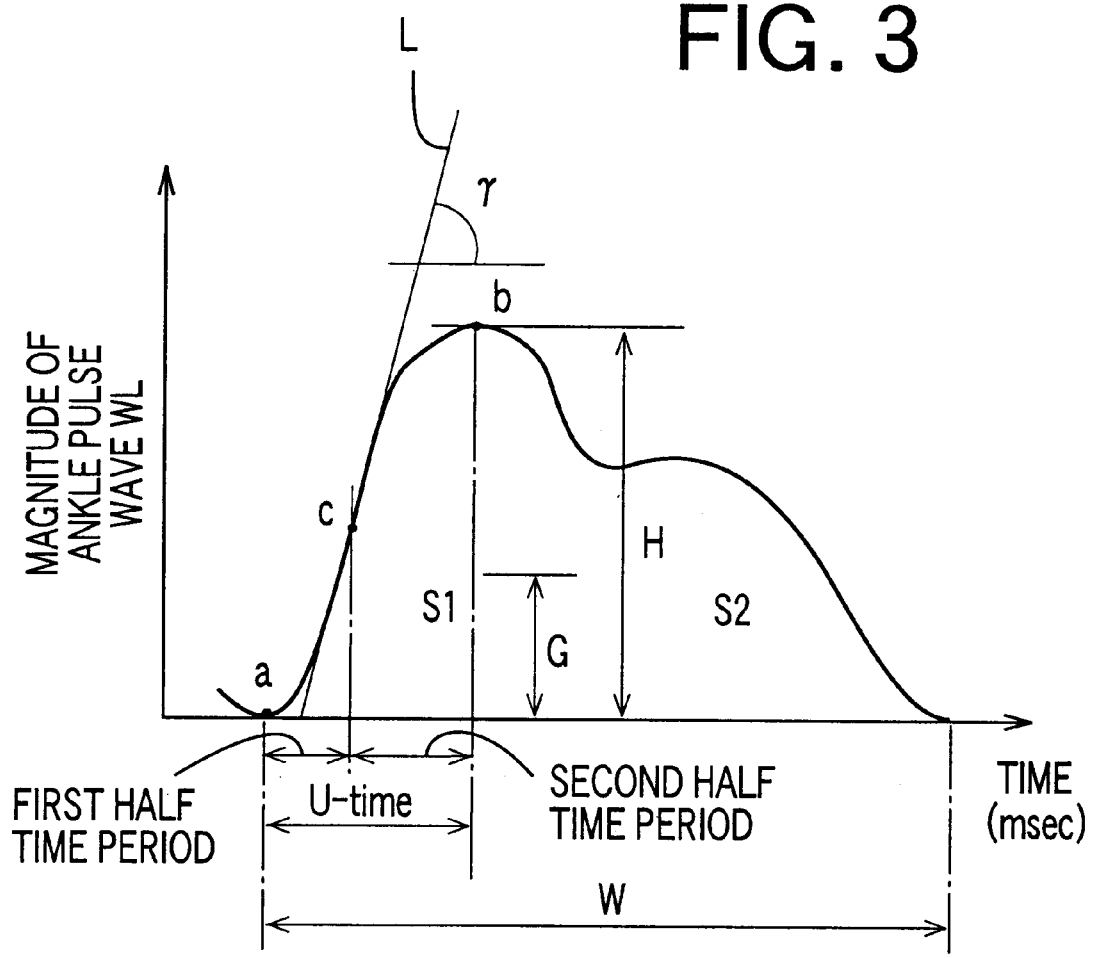
FIG. 3 is a graph showing an example of an ankle pulse wave WL.

An increase-characteristic-value determining means 62 determines a value (hereinafter, referred to as "increase-characteristic value") which is characteristic of an increasing portion (i.e., a portion from a rising point to a peak point) of a heartbeat-synchronous pulse of each of the right-ankle and left ankle pulse waves $WL_R$, $WL_L$ which are extracted by the pulse-wave filter circuits 32c, 32d while the right and left ankle cuffs 18R, 18L are maintained at the pulse-wave-detection pressure by the cuff-pressure changing means 60. FIG. 3 shows an example of an ankle pulse wave WL ($WL_R$ or $WL_L$), and examples, of the above-indicated increase-characteristic value. More specifically described, the increase-characteristic value may be a full time period, U-time (msec), of the increasing portion from the rising point, a, to the peak point, b; a slope, γ, of a tangent line, L, of a greatest-slope point, c, where the increasing portion from the rising point a to the peak point b takes the greatest rate of increase; a first half time period of the increasing portion, measured from the rising point a to the greatest-slope point c; a second half time period of the increasing portion, measured from the greatest-slope point c to the peak point b; or a ratio of the first half time period to the second half time period, or a ratio of the second half time period to the first half time period. As the decree of stenosis of arteries of an upstream-side portion of each inferior limb that is located on an upstream side of each ankle 12R, 12L increases, the slope of the increasing portion of each heartbeat-synchronous pulse of the ankle pulse wave $WL_R$, $WL_L$ decreases. Therefore, if the upstream-side portion of each inferior limb located on the upstream side of each ankle 12R, 12L suffers arteriostenosis, the increase-characteristic value changes with the degree of arteriostenosis. For example, the full time period U-time increases as the degree of arteriostenosis increases. Therefore, the increase-characteristic value determined based on the ankle pulse wave $WL_R$, $WL_L$ is a sort of stenosis-relating pulse-wave information, and the increase-characteristic-value determining means 62 functions as a stenosis-relating-pulse-wave-information obtaining means.

A sharpness-degree determining means 64 determines a degree of sharpness (hereinafter, referred to as "sharpness-degree") of a heartbeat-synchronous pulse of each of the right-ankle and left-ankle pulse waves $WL_R$, $WL_L$ which are extracted by the pulse-wave filter circuits 32c, 32d while the right and left ankle cuffs 18R, 18L are maintained at the pulse-wave-detection pressure by the cuff-pressure changing means 60. The sharpness degree indicates a degree of upward projection of each heartbeat-synchronous pulse of each ankle pulse wave $WL_R$, $WL_L$. The sharpness degree may be a normalized pulse area, VR (=S/(W×H)), which is obtained by dividing a pulse area S (=S1+S2) calculated by summarizing one heartbeat-synchronous pulse of ankle pulse wave WL, shown in FIG. 3, over a pulse period, W, by a product (W×H) of a height, H of the peak point b and the pulse period W; a normalized value of a first-half area S1 calculated by summarizing a first half portion (i.e., the increasing portion) from the rising point a to the peak point b; a normalized value of a second-half area S2 calculated by summarizing a second half portion following the peak point b; or a normalized value, I/W, obtained by dividing, by the pulse period W, a width, I, of one heartbeat-synchronous pulse at a height equal to two thirds, H×(⅔), of the peak-point height H. Otherwise, the normalized pulse area VR may be replaced by a parameter % MAP (=100×G/H) that is obtained as a percentage of a height, G, of a center of gravity of the pulse area S relative to the peak-point height H, i.e., pulse pressure. If the upstream-side portion of each inferior limb located on the upstream side of each ankle 12R, 12L suffers arteriostenosis, the amplitude of each heartbeat-synchronous pulse of the ankle pulse wave $WL_R$, $WL_L$ decreases, and accordingly the sharpness degree of each heartbeat-synchronous pulse decreases. Therefore, the sharpness degree determined based on the ankle pulse wave $WL_R$, $WL_L$ is another sort of stenosis-relating pulse-wave information, and the sharpness-degree determining means 64 functions as the stenosis-relating-pulse-wave-information obtaining means.

A superior-limb-pulse-wave-propagation-velocity-relating-information obtaining means 66 obtains superior-limb-pulse-wave-propagation-velocity-relating information which relates to a velocity at which a pulse wave propagates between two prescribed portions of the patient that include a superior limb of the patient (but do not include the inferior limbs of the patient). The two prescribed portions may be the heart and the upper arm around which the upper-arm cuff 20 is wound. The superior-limb-pulse-wave-propagation-velocity-relating information may be the superior-limb-pulse-wave propagation velocity itself, or a superior-limb-pulse-wave propagation time as a time needed for the superior-limb pulse wave to propagate between the two prescribed portions including the superior limb. In the case where the two prescribed portions are the heart and the upper arm around which the upper-arm cuff 20 is wound, a superior-limb-pulse-wave propagation time, hbDT (sec), is determined as a time difference between a time of detection of a prescribed periodic point (e.g., a starting point of a first heart sound I) of the heart sounds detected by the heart-sound microphone 44 and a time of detection of a corresponding periodic point (e.g., a rising point) of the upper-arm pulse wave WA extracted by the pulse-wave filter circuit 32 functioning as a superior-limb-pulse-wave detecting device, and a superior-limb-pulse-wave propagation velocity, hbPWV (cm/sec), is determined based on the thus determined superior-limb-pulse-wave propagation time hbDT according to the following expression (1) pre-stored in the ROM 50:

$$hbPWV = L1/hbDT \qquad (1)$$

where L1 (cm) is a constant value which is experimentally determined, in advance, to indicate a distance from the aortic valve via the aorta to the position where each upper-arm cuff 20 (20R, 20L) is worn.

An inferior-limb-pulse-wave-propagation-velocity-relating-information obtaining means 68 obtains inferior-limb-pulse-wave-propagation-velocity-relating information which relates to a velocity at which a pulse wave propagates between two prescribed portions of the patient that include an inferior limb of the patient (but do not include the superior limbs of the patient). The two prescribed portions may be the heart and each of the two ankles around which the respective ankle cuffs 18 (18R, 18L) are wound. Like the superior-limb-pulse-wave-propagation-velocity-relating information, the inferior-limb-pulse-wave-propagation-velocity-relating information may be the inferior-limb-pulse-wave propagation velocity itself, or an inferior-limb-pulse-wave propagation time as a time needed for the inferior-limb pulse wave to propagate between the two prescribed portions including the inferior limb. If the patient has arteriostenosis between the two prescribed portions, the inferior-limb-pulse-wave propagation velocity decreases, and the inferior-limb-pulse-wave propagation time increases. Therefore, the inferior-limb-pulse-wave-propagation-velocity-relating information is another sort of stenosis-relating pulse-wave information, and the inferior-limb-pulse-wave-propagation-velocity-relating-information obtaining means 68 is the stenosis-relating-pulse-wave-information obtaining means. In the case where the two prescribed portions are the heart and each of the two ankles around which the two upper-arm cuffs 18 (18R, 18L) are wound, an inferior-limb-pulse-wave propagation time, baDT (sec), is determined as a time difference between a time of detection of a prescribed periodic point (e.g., the starting point of the first heart sound I) of the heart sounds detected by the heart-sound microphone 44 and a time of detection of a corresponding periodic point (e.g., a rising point) of each of the ankle pulse waves WL ($WL_R$, $WL_L$) extracted by the pulse-wave filter circuits 32 (32c, 32d) each functioning as an inferior-limb-pulse-wave detecting device, and an inferior-limb-pulse-wave propagation velocity, baPWV (cm/sec), is determined based on the thus determined inferior-limb-pulse-wave propagation time baDT according to the following expression (2) pre-stored in the ROM 50:

$$baPWV = L2/baDT \qquad (2)$$

where L2 (cm) is a constant value which is experimentally determined, in advance, to indicate a distance from the aortic valve via the aorta to the position where each ankle cuff 18 (18R, 18L) is worn.

Otherwise, the two prescribed portions may be each of the upper arms around which the respective upper-arm cuffs 20 (20R, 20L) are wound, and each of the two ankles around which the respective ankle cuffs 18 (18R, 18L) are wound. In this case, an inferior-limb-pulse-wave propagation time, baDT (sec), is determined as a time difference between a time of detection of a prescribed periodic point (e.g., the rising point) of each of the upper-arm pulse waves WA ($WA_R$, $WA_L$) extracted by the pulse-wave filter circuits 32 (32a, 32b) each functioning as a superior-limb-pulse-wave detecting device, and a time of detection of a corresponding periodic point (e.g., a rising point) of each of the ankle pulse waves WL ($WL_R$, $WL_L$) extracted by the pulse-wave filter circuits 32 (32c, 32d) each functioning as an inferior-limb-pulse-wave detecting device, and an inferior-limb-pulse-wave propagation velocity, baPWV (cm/sec), is determined based on the thus determined inferior-limb-pulse-wave propagation time baDT according to the following modified expression (2') pre-stored in the ROM 50:

$$baPWV = L2'/baDT \qquad (2')$$

where L2' (cm) is a constant value which is experimentally determined, in advance, to indicate a difference between the respective distances from the heart to the respective positions where each upper-arm cuff 20 (20R, 20L) is worn and each ankle cuff 18 (18R, 18L) is worn.

Figure 4:
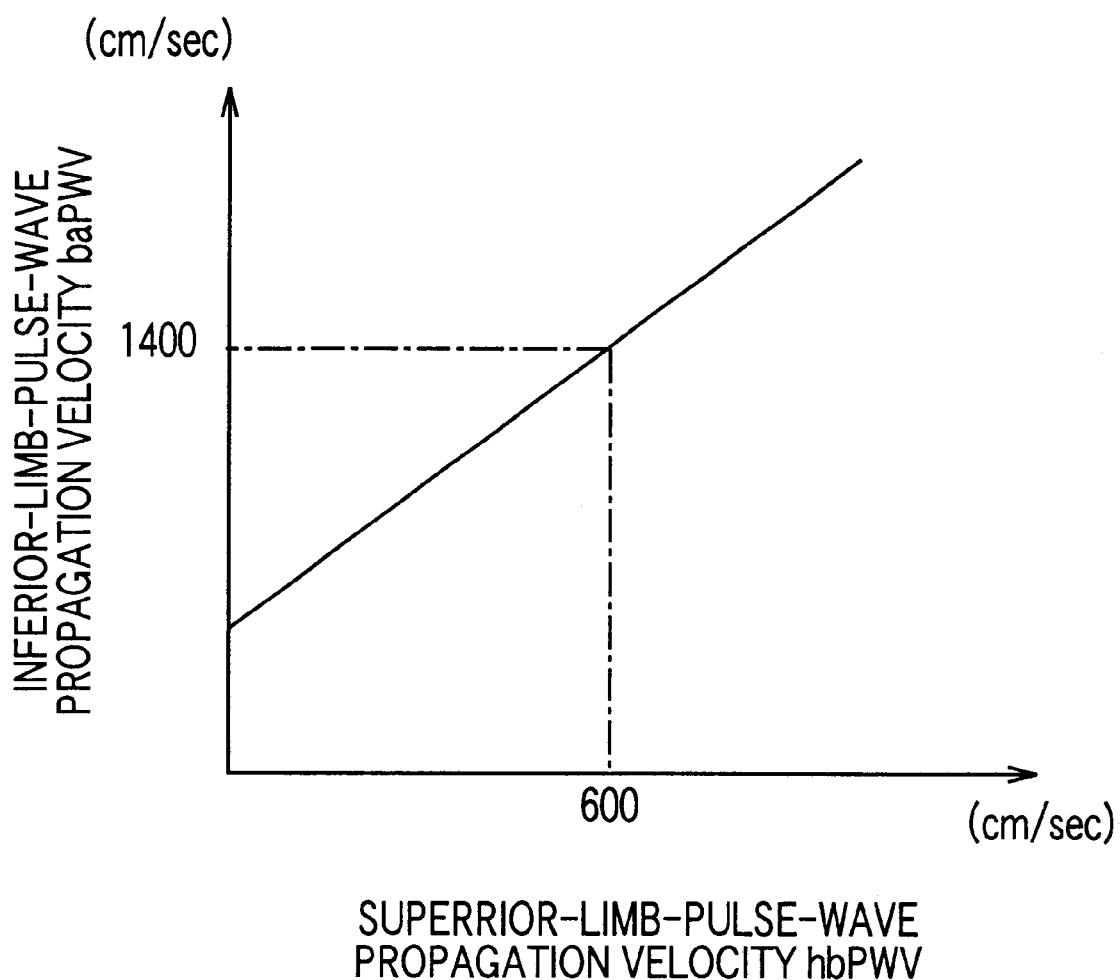
FIG. 4 is a graph showing an example of a relationship between a superior-limb-pulse-wave propagation velocity hbPW, determined between heart and upper arm, and an inferior-limb-pulse-wave propagation velocity baPW, determined between heart and ankle.

A normal-range determining means 70 determines, based on the superior-limb-pulse-wave-propagation-velocity-relating information obtained by the superior-limb-pulse-wave-propagation-velocity-relating-information obtaining means 66, a normal range of inferior-limb-pulse-wave-propagation-velocity-relating information, according to a predetermined relationship between inferior-limb-pulse-wave-propagation-velocity-relating information and superior-limb-pulse-wave-propagation-velocity-relating information. The relationship is pre-stored in the ROM 50. In the case where neither the superior limbs nor the inferior limbs have arteriostenosis, there is a proportional relationship between inferior-limb-pulse-wave-propagation-velocity-relating information and superior-limb-pulse-wave-propagation-velocity-relating information. Therefore, on an assumption that the superior limbs do not have arteriostenosis, the normal-range determining means 70 determines the normal range based on the superior-limb-pulse-wave-propagation-velocity-relating information actually obtained by the superior-limb-pulse-wave-propagation-velocity-relating-information obtaining means 66, according to the predetermined relationship. FIG. 4 shows an example of a relationship between inferior-limb-pulse-wave propagation velocity baPWV determined between heart and ankle, and superior-limb-pulse-wave propagation velocity hbPWV determined between heart and upper arm. In the case where the relationship shown in FIG. 4 is used as the predetermined relationship, the normal range may be determined such that the normal range ranges from −10% of an inferior-limb-pulse-wave propagation velocity baPWV corresponding to the actual superior-limb-pulse-wave propagation velocity hbPWV to +10% of the same velocity baPWV. The reason why FIG. 4 shows that the inferior-limb-pulse-wave propagation velocity baPWV is higher than the superior-limb-pulse-wave propagation velocity hbPWV, is that pulse-wave propagation velocity PWV is inversely proportional to the square root of diameter of artery and the diameter of artery of the ankle is smaller than that of the upper arm.

An upper-arm-blood-pressure determining means 72 determines BP values of the right upper arm 14R, i.e., a right-upper-arm systolic BP value $BP_{ASYS}(R)$, a right-upper-arm diastolic BP value $BP_{ADIA}(R)$, and a right-upper-arm mean BP value $BP_{AMEAN}(R)$, and BP values of the left upper arm 14L, i.e., a left-upper-arm systolic BP value $BP_{ASYS}(L)$, a left-upper-arm diastolic BP value $BP_{ADIA}(L)$, and a left-upper-arm mean BP value $BP_{AMEAN}(L)$, according to well-known oscillometric method, based on the change of respective amplitudes of the heartbeat-synchronous pulses of the pulse wave $WA_R$ represented by the pulse-wave signal $SM_a$ detected one by one during the slow deflation of the right upper-arm cuff 20R under the control of the cuff-pressure changing means 60 and based on the change of respective amplitudes of the heartbeat-synchronous pulses of the pulse wave $WA_L$ represented by the pulse-wave signal $SM_b$ detected one by one during the slow deflation of the left upper-arm cuff 20L under the control of the means 60. In addition, the determining means 72 operates the display device 54 to display the thus determined BP values $BP_{ASYS}(R)$, $BP_{ASYS}(L)$, etc.

A relative-value determining means 74 determines a relative value between the left-inferior-limb pulse-wave-propagation-velocity-relating information and the right-inferior-limb pulse-wave-propagation-velocity-relating information which are obtained by the inferior-limb-pulse-wave-propagation-velocity-relating-information obtaining means 68, determines a relative value between the left-inferior-limb increase-characteristic value and the right-inferior-limb increase-characteristic value which are determined by the increase-characteristic-value determining means 62, and determines a relative value between the left-inferior-limb sharpness degree and the right-inferior-limb sharpness degree which are determined by the sharpness-degree determining means 64. Each of the above-indicated three sorts of relative values indicates a difference between the two pieces of stenosis-relating pulse-wave information (e.g., pulse-wave-propagation-velocity-relating information) obtained from the left and right inferior limbs, respectively, and may be a difference of the two pieces of information, or a ratio of one of the two pieces of information to the other piece of information.

A preliminary-judgment making means 76 makes a preliminary judgment that the artery of the left or right inferior limb is suspected of stenosis, if at least one of the left-inferior-limb or right-inferior-limb pulse-wave-propagation-velocity-relating information obtained by the inferior-limb-pulse-wave-propagation-velocity-relating-information obtaining means 68, the left-inferior-limb or right-inferior-limb increase-characteristic value determined by the increase-characteristic-value determining means 62, and the left-inferior-limb or right-inferior-limb sharpness degree determined by the sharpness-degree determining means 64 falls in a corresponding one of three abnormal ranges respectively predetermined for the three sorts of stenosis-relating pulse-wave information. Each of the three means 68, 62, 64 functions as the stenosis-relating-pulse-wave-information obtaining means.

The abnormal range predetermined for the inferior-limb-pulse-wave-propagation-velocity-relating information is the range outside the normal range determined in advance by the normal-range determining means 70. The respective abnormal ranges for the increase-characteristic value and the sharpness degree are experimentally determined in advance. In the case where the full time period U-time is determined as the increase-characteristic value, the abnormal range may be a range not smaller than 180 msec; and in the case where the parameter % MAP is determined as the sharpness degree, the abnormal range may be a range not greater than 42%. Alternatively, the preliminary-judgment making means 76 may be so modified as to make the preliminary judgment that the artery of the left or right inferior limb is suspected of stenosis, if at least two, or all, of the left-inferior-limb or right-inferior-limb pulse-wave-propagation-velocity-relating information, the left-inferior-limb or right-inferior-limb increase-characteristic value, and the left-inferior-limb or right-inferior-limb sharpness degree falls in corresponding two, or all, of the three abnormal ranges. Since each of the pulse-wave-propagation-velocity-relating information, the increase-characteristic value, and the limb sharpness degree is obtained or determined for each of the left and right inferior limbs, the means 76 can make a preliminary judgment about whether each one of the left and right inferior limbs is suspected of arteriostenosis.

The preliminary-judgment making means 76 additionally makes a preliminary judgment that the artery of the left or right inferior limb is suspected of stenosis, if at least one of the relative value of the inferior-limb-pulse-wave-propagation-velocity-relating information, the relative value of the increase-characteristic value, and the relative value of the limb sharpness, each determined by the relative-value determining means 74, is greater than a corresponding one of three reference values respectively predetermined for the three sorts of relative values. If the relative value is greater than the corresponding reference value, it can be speculated that either one of the left and right inferior limbs suffers arteriostenosis. In this case, however, the means 76 cannot make a preliminary judgment about which one of the two inferior limbs is suspected of arteriostenosis.

If the above-indicated inferior-limb-pulse-wave-propagation-velocity-relating information, increase-characteristic value, and limb sharpness do not fall in the respective abnormal ranges and the respective relative values of the pulse-wave-propagation-velocity-relating information, increase-characteristic value, and limb sharpness are not greater than the respective reference values, the preliminary-judgment making means 76 additionally judges whether the left-upper-arm or right-upper-ram blood pressure $BP_{ASYS}$ determined by the upper-arm-blood-pressure determining means 72 is lower than a preset lower-limit value (e.g., 100 mmHg). A positive judgment made by the means 76 indicates that there is possibility that the upper-arm blood pressure $BP_{ASYS}$ is excessively low because the upper arm suffers >-1 arteriostenosis. If the upper arm has arteriostenosis as well, it is difficult to make a diagnosis on the arteriostenosis of inferior limb based on the index ABI measured by the present apparatus 10.

An ABI-measurement starting means 78 functioning as a blood-pressure-measurement starting means starts, if the preliminary-judgment making means 76 makes the judgment that the artery of at least one of the left and right inferior limbs is suspected of stenosis, the upper-arm-blood-pressure determining means 72 to determine BP values of each of the left and right upper arms 14L, 14R, and starts an ankle-blood-pressure determining means 82, described later, to determine BP values of a corresponding one of the left and right ankles 12L, 12R. Thus, in the case where only one of the two inferior limbs is suspected of stenosis, the ankle-blood-pressure determining means 82 determines the BP values of the one ankle 12L or 12R only. The upper-arm-blood-pressure determining means 72 may be modified such that in this case, the means 72 determines the BP values of only a pre-selected one of the two upper arms 14L, 14R.

An inferior-limb-blood-pressure-measurement starting means 80 starts, if the preliminary-judgment making means 76 makes the judgment that the artery of at least one of the left and right inferior limbs is suspected of stenosis and the upper-arm systolic blood pressure $BP_{ASYS}$ is smaller than the lower-limit value, the ankle-blood-pressure determining means 82 to determine BP values $BP_L$ (e.g., $BP_{LSYS}$, $BP_{LDIA}$, $BP_{LMEAN}$) of a corresponding one of the left and right ankles 12L, 12R. In the case where the upper-arm systolic blood pressure $BP_{ASYS}$ is smaller than the lower-limit value, it is difficult to make a diagnosis on the stenosis of inferior-limb artery based on the index ABI. Therefore, the diagnosis of stenosis of inferior-limb artery is made based on the ankle blood-pressure values $BP_L$.

Figure 5:
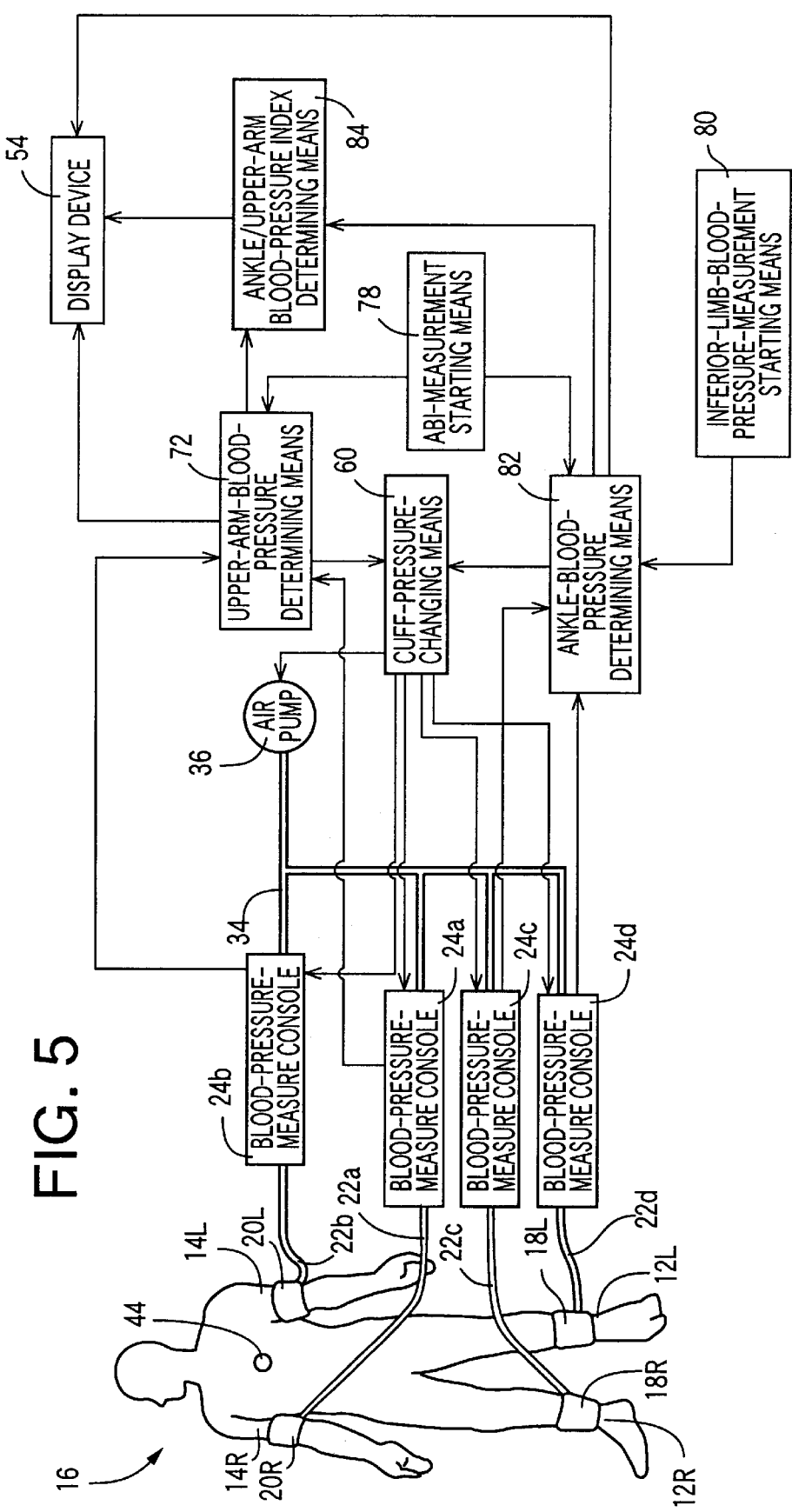
FIG. 5 is a diagrammatic view for explaining additional essential functions of the control device of the apparatus of FIG. 1 that are operated when the control functions shown in FIG. 2 provide the preliminary judgment that an inferior-limb artery of the patient is suspected of stenosis.

FIG. 5 shows a diagrammatic view for explaining additional essential functions of the control device 38 that are operated when the functions shown in FIG. 2 provide the judgment that the inferior-limb artery of the patient is suspected of stenosis.

The ankle-blood-pressure determining means 82 is started by the ABI-measurement starting means 78 or the inferior-limb-blood-pressure-measurement starting means 80, and operates the cuff-pressure changing means 60 to change the air pressure of at least one of the right and left ankle cuffs 18R, 18L that is wound around at least one of the right and left inferior limbs (i.e., the right and left ankles 12R, 12L) that is suspected of arteriostenosis. The determining means 82 determines BP values of the right ankle 12R, i.e., a right-ankle systolic BP value $BP_{LSYS}(R)$, a right-ankle diastolic BP value $BP_{LDIA}(R)$, and a right-ankle mean BP value $BP_{LMEAN}(R)$, and BP values of the left ankle 12L, i.e., a left-ankle systolic BP value $BP_{LSYS}(L)$, a left-ankle diastolic BP value $BP_{LDIA}(L)$, and a left-ankle mean BP value $BP_{LMEAN}(L)$, according to well-known oscillometric method, based on the change of respective amplitudes of the heartbeat-synchronous pulses of the pulse wave $WL_R$ represented by the pulse-wave signal $SM_c$ detected one by one during the slow deflation of the right ankle cuff 18R under the control of the cuff-pressure changing means 60 and based on the change of respective amplitudes of the heartbeat-synchronous pulses of the pulse wave $WL_L$ represented by the pulse-wave signal $SM_d$ detected one by one during the slow deflation of the left ankle cuff 18L under the control of the means 60. In addition, the determining means 82 operates the display device 54 to display the thus determined BP values $BP_{LSYS}(R)$, $BP_{LSYS}(L)$, etc.

An ankle/upper-arm BP index determining means 84 functioning as the superior-and-inferior-limb BP index determining means determines a right ankle/upper-arm BP index (=ABIR), or a left ankle/upper-arm BP index (=ABIL), by dividing the right ankle blood pressure $BP_L(R)$ (e.g., the right ankle systolic blood pressure $BP_{LSYS}(R)$), or the left ankle blood pressure $BP_L(L)$ (e.g., the left ankle systolic blood pressure $BP_{LSYS}(L)$), determined by the ankle-blood-pressure determining means 82, by the upper-arm blood pressure $BP_A$ corresponding to the ankle blood pressure $BP_L$ (e.g., the upper-arm systolic blood pressure $BP_{ASYS}$ corresponds to the ankle systolic blood pressure $BP_{LSYS}$) determined by the upper-arm-blood-pressure determining means 72. The determining means 84 operates the display device 54 to display the thus determined index values ABIR, ABIL.

If the right or left inferior limb suffers arteriostenosis, the right-ankle or left-ankle blood pressure $BP_L(R)$, $BP_L(L)$ takes a lowered value and accordingly the right or left index ABIR, ABIL takes a decreased value. Therefore, if the right or left index ABIR, ABIL is smaller than a reference value (e.g., 0.9), it can be judged that the right or left inferior limb is strongly suspected of arteriostenosis. Meanwhile, it is preferred that the higher one of the right-upper-arm and left-upper-arm blood pressure values $BP_A$ (R), $BP_A$ (L) be used as the upper-arm blood pressure $BP_A$ to be used in determining the index values ABIR, ABIL. However, it is possible to select, before the blood-pressure measuring operation, one of the right-upper-arm and left-upper-arm blood pressure values $BP_A$ (R), $BP_A$ (L) that is to be used for this purpose. Since the higher one of the two upper-arm blood pressure values is used, smaller index values ABI are obtained, which leads to be more likely to find the stenosis of inferior-limb artery.

Figure 6:
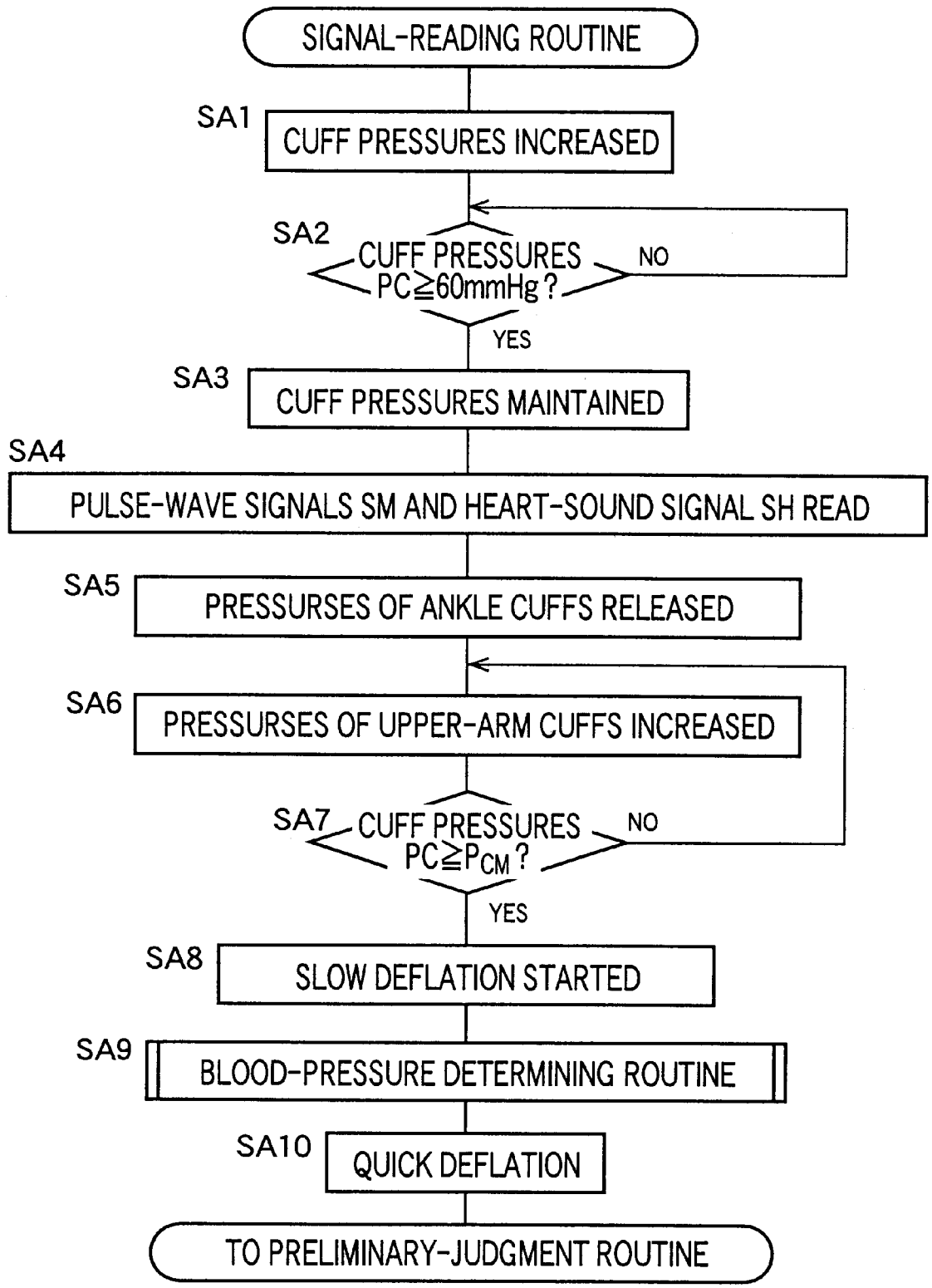
FIG. 6 is a flow chart representing a signal-reading routine according to which the control functions of the control device, shown in FIGS. 2 and 5, are operated to read signals needed to provide a preliminary judgment.
Figure 7:
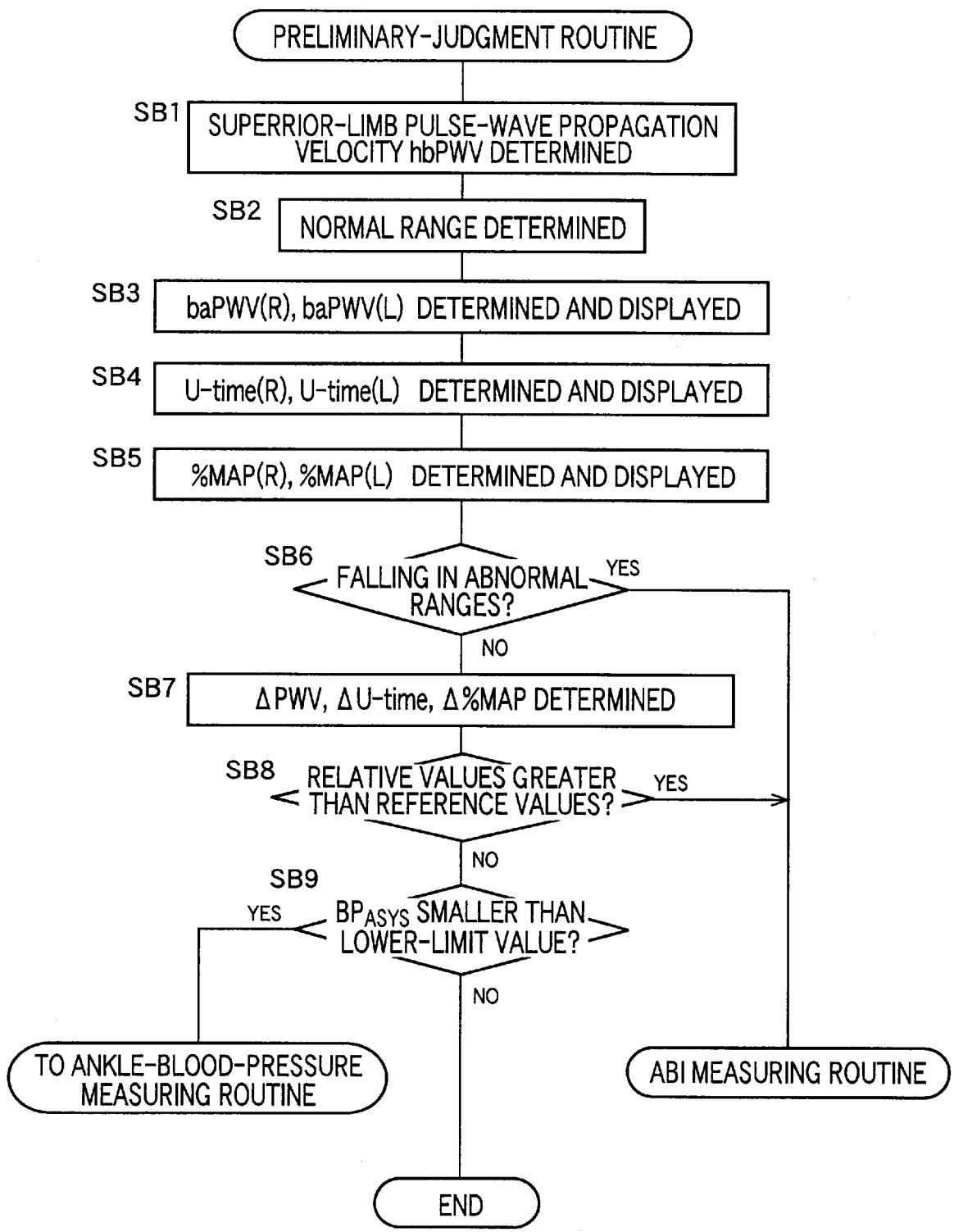
FIG. 7 is a flow chart representing a preliminary judgment routine according to which the control functions of the control device, shown in FIGS. 2 and 5, are operated to provide the preliminary judgment based on the signals read according to the signal-reading routine of FIG. 6.
Figure 8:
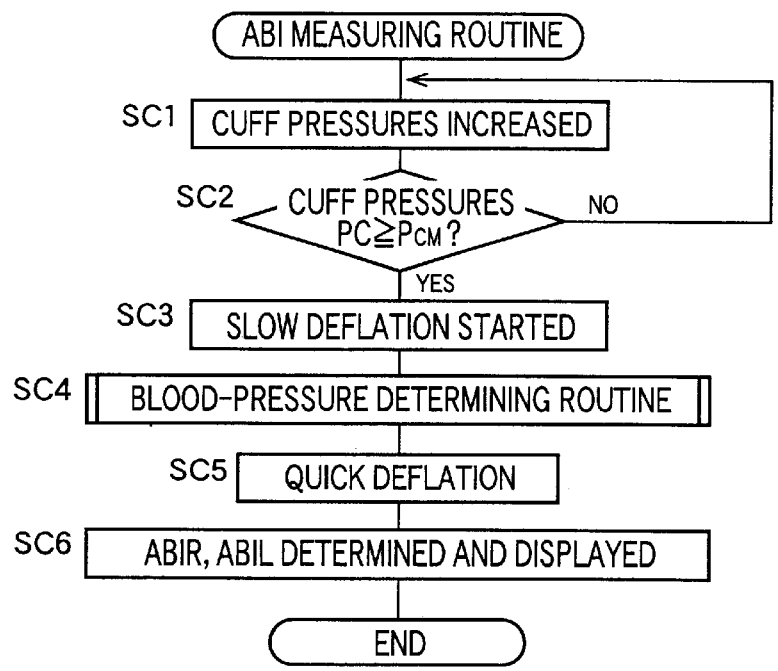
FIG. 8 is a flow chart representing an ABI measuring routine according to which the control functions of the control device, shown in FIGS. 2 and 5, are operated to measure an index ABI of the patient.
Figure 9:
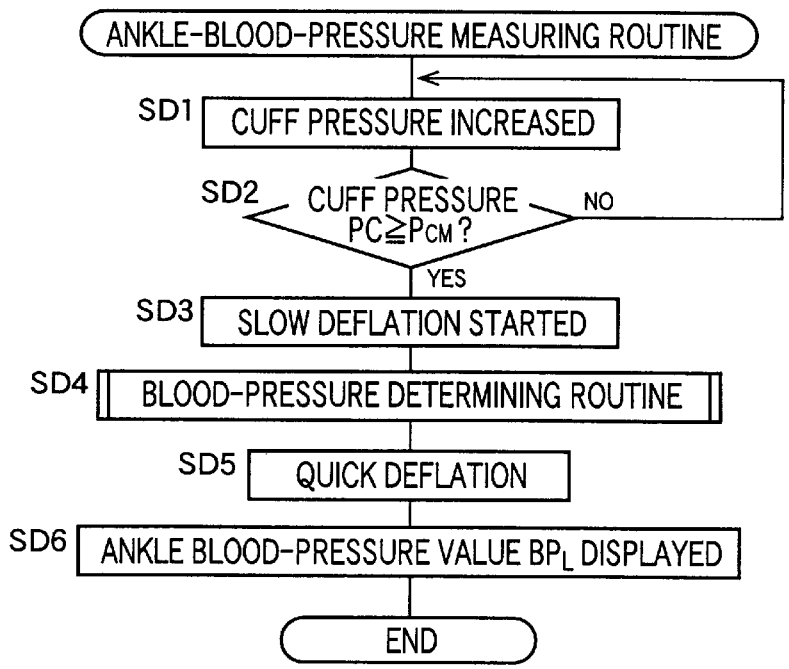
FIG. 9 is a flow chart representing an ankle-blood-pressure-measuring routine according to which the control functions of the control device, shown in FIGS. 2 and 5, are operated to measure an ankle blood pressure of the patient.

FIGS. 6 to 9 are flow charts representing control programs according to which the control functions of the control device 38, shown in FIGS. 2 and 5, are operated. FIG. 6 shows a signal-reading routine to read the signals needed to make a preliminary judgment; FIG. 7 shows a preliminary-judgment routine to make the preliminary judgment based on the signals read; FIG. 8 shows an ABI measuring routine; and FIG. 9 shows an ankle-blood-pressure measuring routine.

First, the signal-reading routine of FIG. 6 will be described. At Step SA1 of FIG. 6 (hereinafter, "Step" is omitted, if appropriate), the control device 38 switches the respective pressure control valves 26 (26a, 26b, 26c, 26d) of the four blood-pressure-measure consoles 24a, 24b, 24c, 24d to their pressure-supply positions, and operates the air pump 36, so as to start increasing the respective pressures PC of the two ankle cuffs 18R, 18L and the two upper-arm cuffs 20R, 20L. Then, at SA2, the control device 38 judges whether the respective pressures PC of the four cuffs 18R, 18L, 20R, 20L have reached the pulse-wave-detection pressure, e.g., 60 mmHg. If a negative judgment is made at SA2, SA2 is repeated.

Meanwhile, if a positive judgment is made at SA2, the control goes to SA3 to stop the air pump 36 and switch the four control valves 26 to their pressure-maintain positions, so that the four cuff pressures PC are maintained at the pulse-wave-detection pressure. SA1, SA2, and SA3 correspond to the cuff-pressure changing means 60.

Then, at SA4, the control device 38 reads in respective lengths of the respective pulse-wave signals $SM_b$, $SM_c$, $SM_d$ supplied from the respective pulse-wave filter circuits 32b, 32c, 32d of the three blood-pressure-measure consoles 24b, 24c, 24d, the lengths each corresponding to one heartbeat of the patient. In addition, the control device 38 reads in a length of the heart-sound signal SH, supplied from the heart-sound microphone 44, that corresponds to the same one heartbeat.

Then, the control goes to SA5, SA6, SA7, and SA8 corresponding to the cuff-pressure changing means 60. At SA5, the control device 38 switches the two control valves 26c, 26d to their quick-deflation positions, so that the respective pressures $PC_c$, $PC_d$ of the two ankle cuffs 18R, 18L are released. At SA6, the control device 38 switches the two control valves 26a, 26b to their pressure-supply positions, again, and operates the air pump 36, again, so as to start increasing the respective pressures $PC_a$, $PC_b$ of the upper-arm cuffs 20R, 20L. At SA7, the control device 38 judges whether the respective pressures $PC_a$, $PC_b$ of the upper-arm cuffs 20R, 20L have reached the first target pressure $P_{CM}$, e.g., 180 mmHg. If a negative judgment is made at SA7, SA6 and SA7 are repeated, while the pressures $PC_a$, $PC_b$ are continuously increased.

Meanwhile, if a positive judgment is made at SA7, the control goes to SA8 to stop the air pump 36 and switch the two control valves 26a, 26b to their slow-deflation positions, so that the respective pressures $PC_a$, $PC_b$ of the upper-arm cuffs 20R, 20L are slowly decreased at the prescribed rate, e.g., 5 mmHg/sec.

Next, the control goes to SA9, i.e., a blood-pressure-determining routine corresponding to the upper-arm-blood-pressure determining means 72. More specifically described, the control device 38 determines respective amplitudes of respective heartbeat-synchronous pulses of each of the upper-arm pulse waves $WA_R$, $WA_L$ represented by the pulse-wave signals $SM_a$, $SM_b$ continuously supplied from the pulse-wave filter circuits 32a, 32b, and determines a right-upper-arm systolic blood pressure $BP_{ASYS}(R)$, etc. and a left-upper-arm systolic blood pressure $BP_{ASYS}(L)$, etc., according to well-known oscillometric blood-pressure determining algorithm, based on the change of the determined amplitudes of the right-upper-arm pulse wave $WA_R$ and the determined amplitudes of the left-upper-arm pulse wave $WA_L$.

Then, at SA10 corresponding to the cuff-pressure changing means 60, the control device 38 switches the two control valves 26a, 26b to their quick-deflation positions, so that the respective pressures $PC_a$, $PC_b$ of the upper-arm cuffs 20R, 20L are quickly decreased. Thus, the signal-reading routine is finished.

The signal-reading routine is followed by the preliminary-judgment routine of FIG. 7. First, the control device 38 carries out at SB1 corresponding to the superior-limb-pulse-wave-propagation-velocity-relating-information obtaining means 66. More specifically described, at SB1, the control device 38 determines a starting point of a first heart sound I on the one-heartbeat length of the heart-sound signal SH, read at SA4 of FIG. 6, and determines a rising point of the one-heartbeat length (i.e., one-heartbeat-synchronous pulse) of the left-upper-ram pulse wave $WA_L$ represented by the pulse-wave signal $SM_b$ read at SA4. In addition, the control device 38 determines, as a superior-limb-pulse-wave propagation time hbDT, a time difference between the time of detection of the starting point of the first heart sound I and the time of detection of the rising point of the left-upper-arm pulse wave $WA_L$, and determines a superior-limb-pulse-wave propagation velocity hbPWV by replacing the parameter hbDT of the previously-explained expression (1) with the thus determined superior-limb-pulse-wave propagation time.

Next, the control goes to SB2 corresponding to the normal-range determining means 70. At SB2, the control device 38 determines, based on the superior-limb-pulse-wave propagation velocity hbPWV determined at SB1, an inferior-limb-pulse-wave propagation velocity baPWV, according to the relationship shown in FIG. 4, and determines, based on the thus determined inferior-limb-pulse-wave propagation velocity baPW, a normal range of inferior-limb-pulse-wave propagation velocity baPWV that ranges from −10% of the thus determined velocity baPWV to +10% of the same determined velocity baPW.

Then, the control goes to SB3 corresponding to the inferior-limb-pulse-wave-propagation-velocity-relating-information obtaining means 68, to determine a right-inferior-limb pulse-wave propagation velocity baPWV(R) and a left-inferior-limb pulse-wave propagation velocity baPWV(L). More specifically described, at SB3, the control device 38 determines a rising point of the one-heartbeat length (i.e., one-heartbeat-synchronous pulse) of each of the right-ankle pulse wave $WL_R$ and the left-ankle pulse wave $WL_L$ represented by the pulse-wave signals $SM_c$, $SM_d$ read at SA4. In addition, the control device 38 determines, as a right-inferior-limb pulse-wave propagation time baDT(R), a time difference between the time of detection of the rising point of the left-upper-arm pulse wave $WA_L$ determined at SB1 and the time of detection of the rising point of the right-ankle pulse wave $WL_R$, and determines, as a left-inferior-limb pulse-wave propagation time baDT(L), a time difference between the time of detection of the rising point of the left-upper-arm pulse wave $WA_L$ determined at SB1 and the time of detection of the rising point of the left-ankle pulse wave $WL_L$. Moreover, the control device 38 determines the right-inferior-limb pulse-wave propagation velocity baPWV(R) by replacing the parameter baDT of the previously-explained modified expression (2') with the thus determined right-inferior-limb pulse-wave propagation time baDT(R), and determines the left-inferior-limb pulse-wave propagation velocity baPWV(L) by replacing the parameter baDT of the previously-explained expression (2) with the thus determined left-inferior-limb pulse-wave propagation time baDT(L). The control device 38 operates the display device 54 to display the thus determined right-inferior-limb pulse-wave propagation velocity baPWV(R) and left-inferior-limb pulse-wave propagation velocity baPWV(L).

Next, the control goes to SB4 corresponding to the increase-characteristic-value determining means 62. At SB4, the control device 38 determines a rising point and a peak point of the one-heartbeat length (i.e., one-heartbeat-synchronous pulse) of each of the right-ankle pulse wave $WL_R$ and the left-ankle pulse wave $WL_L$ represented by the pulse-wave signals $SM_c$, $SM_d$ read at SA4 of FIG. 6. In addition, the control device 38 determines, as a right-ankle full time period U-time(R), a time difference between the respective times of detection of the rising point and the point point of the right-ankle pulse wave $WL_R$, and determines, as a left-ankle full time period U-time(L), a time difference between the respective times of detection of the rising point and the peak point of the left-ankle pulse wave $WL_L$. The control device 38 operates the display device 54 to display the thus determined right-ankle full time period U-time(R) and left-ankle full time period U-time(L).

Then, the control goes to SB5 corresponding to the sharpness-degree determining means 64. At SB5, the control device 38 determines, based on the one-heartbeat length (i.e., one-heartbeat-synchronous pulse) of the right-ankle pulse wave $WL_R$ represented by the pulse-wave signal $SM_c$ read at SA4 of FIG. 6, a right-ankle parameter % MAP(R) by dividing the pulse area S of the one pulse by the product (W×H) of the peak-point height H and the pulse period W. Similarly, the control device 38 determines, based on the one-heartbeat length (i.e., one-heartbeat-synchronous pulse) of the left-ankle pulse wave $WL_L$ represented by the pulse-wave signal $SM_d$ read at SA4 of FIG. 6, a left-ankle parameter % MAP(L) by dividing the pulse area S of the one pulse by the product (W×H) of the peak-point height H and the pulse period W. The control device 38 operates the display device 54 to display the thus determined right-ankle parameter % MAP(R) and left-ankle parameter % MAP(L).

Then, at SB6, the control device 38 judges whether each of the right-inferior-limb pulse-wave propagation velocity baPWV(R) and the left-inferior-limb pulse-wave propagation velocity baPWV(L), determined at SB3, the two full time periods U-time(R), U-time(L) determined at SB4, and the two parameter values % MAP(R), % MAP(L) determined at SB5, falls in a corresponding one of predetermined abnormal ranges. More specifically described, the control device 38 judges whether each of the right-inferior-limb pulse-wave propagation velocity baPWV(R) and the left-inferior-limb pulse-wave propagation velocity baPWV(L) falls outside the normal range determined at SB2; judges whether each of the two full time periods U-time(R), U-time (L) is longer than 180 msec; and judges whether each of the two parameter values % MAP(R), % MAP(L) is smaller than 42%. If at least one of the above-indicated values baPWV(R), baPWV(L), U-time(R), U-time(L), % MAP(R), % MAP(L) falls in the corresponding one of the abnormal ranges, a positive judgment is made at SB6. Since the positive judgment indicates that the right or left inferior limb is suspected of arteriostenosis, the control goes to the ABI-measuring routine of FIG. 8. On the other hand, if a negative judgment is made at SB6, the control goes to SB7 corresponding to the relative-value determining means 74.

At SB7, the control device 38 determines an absolute value Δ PWV of difference of the right-inferior-limb pulse-wave propagation velocity baPWV(R) and the left-inferior-limb pulse-wave propagation velocity baPWV(L) determined at SB3, as the relative value between those two velocities, an absolute value Δ U-time of difference of the two full time periods U-time(R), U-time(L) determined at SB4, as the relative value of those two periods, and an absolute value Δ % MAP of difference of the two parameter values % MAP(R), % MAP(L) as the relative value between those two values.

Then, at SB8, the control device 38 judges whether each of the three absolute values Δ PWV, Δ U-time, A % MAP is greater than a corresponding one of prescribed reference values. If at least one of the three absolute values Δ PV, Δ U-time, Δ % MAP is greater than the corresponding one of the prescribed reference values, a positive judgment is made at SB8. Since the positive judgment indicates that either one of the two inferior limbs is suspected of arteriostenosis, the control goes to the ABI-measuring routine of FIG. 8 to measure both a right and a left index value ABI. Since the ABI-measuring routine is carried out when a positive judgment is made at SB6 or SB8, SB6 and SB8 correspond to the ABI-measurement starting means 78.

On the other hand, if a negative judgment is made at SB8, the control goes to SB9 to judge whether the upper-arm systolic blood pressure $BP_{ASYS}$ determined at SA9 of FIG. 6 is smaller than the prescribed lower-limit value, e.g., 100 mmHg. If a positive judgment is made at SB9, the control goes to the ankle-blood-pressure measuring routine of FIG. 9. Thus, SB9 corresponds to the inferior-limb-blood-pressure-measurement starting means 80. On the other hand, if a negative judgment is made at SB9, indicating that the inferior limbs are not suspected of arteriostenosis, the present routine is finished without carrying out the ABI-measuring routine or the ankle-blood-pressure measuring routine. Since it is judged at SB6, SB8, or SB9 whether at least one inferior limb is suspected of arteriostenosis, SB6, SB8, and SB9 correspond to the preliminary-judgment making means 76.

Next, the ABI-measuring routine of FIG. 8 will be described. First, the control device 38 carries out SC1, SC2, and SC3 corresponding to the cuff-pressure changing means 60. At SC1, the control device 38 switches the two pressure control valves 26a, 26b connected to the two upper-arm cuffs 20R, 20L, and one or two pressure control valves 26c, 26d connected to one or two ankle cuffs 18R, 18L wound around one or two inferior limbs which has or have been judged, at SB6 or SB8 of FIG. 7, as being suspected of arteriostenosis (in particular, both the two pressure control valves 26c, 26d if at least one of the two inferior limbs has been judged, at SB8, as being suspected of arteriostenosis), to their pressure-supply positions, and operates the air pump 36, so that the respective pressures of the two upper-arm cuffs 20R, 20L and one or two ankle cuffs 18R, 18L are quickly increased. At SC2, the control device 38 judges whether the respective pressures $PC_a$, $PC_b$ of the upper-arm cuffs 20R, 20L have reached the first target pressure $P_{CM}$, e.g., 180 mmHg, and whether the pressure or pressures PC of the one or two ankle cuffs 18R, 18L has or have reached the second target pressure $P_{CM}$, e.g., 240 mmHg. If a negative judgment is made at SC2, SC1 and SC2 are repeated while the respective cuff pressures PC are continuously increased.

Meanwhile, if a positive judgment is made at SC2, the control goes to SC3 to switch the pressure control valves 26 connected to the cuffs 18, 20 whose pressures PC have reached the first or second target pressure $P_{CM}$, to their slow-deflation positions, so that the pressures PC of the cuffs 18, 20 are slowly decreased at the prescribed rate of 5 mmHg/sec. If a positive judgment is made for each of the cuff pressures PC at SC2, the air pump 36 is stopped.

Next, the control goes to SC4 corresponding to the superior-limb-blood-pressure determining means 72 and the ankle-blood-pressure determining means 82. More specifically described, the control device 38 determines respective amplitudes of respective heartbeat-synchronous pulses of each of the upper-arm and ankle pulse waves WA, WL represented by the pulse-wave signals SM continuously supplied from the pulse-wave filter circuits 32, and determines a right-upper-arm systolic blood pressure $BP_{ASYS}(R)$, etc., a left-upper-arm systolic blood pressure $BP_{ASYS}(L)$, etc., and a right-ankle and/or a left-ankle systolic blood pressure $BP_{LSYS}$, according to well-known oscillometric blood-pressure determining algorithm, based on the change of the determined amplitudes of the right-upper-arm pulse wave $WA_R$, the change of the determined amplitudes of the left-upper-arm pulse wave $WA_L$, and the change of the determined amplitudes of the right-ankle or left-ankle pulse wave WL.

Then, at SC5 corresponding to the cuff-pressure changing means 60, the control device 38 switches the pressure control valves 26 to their quick-deflation positions, so that the respective pressures PC of the cuffs 18, 20 are quickly decreased.

Then, the control goes to SC6 corresponding to the ankle/upper-arm BP index determining means 84. At SC6, the control device 38 calculates an index ABIR or ABIL by dividing the right-ankle systolic BP value $BP_{LSYS}(R)$ or the left-ankle systolic BP value $BP_{LSYS}(L)$ determined at SC4, by the higher one of the right-upper-arm systolic blood pressure $PB_{ASYS}$ (R) and the left-upper-arm systolic blood pressure $PB_{ASYS}$ (L) determined at SC4, and operates the display device 54 to display the thus determined index value or values ABIR, ABIL.

Next, the ankle-blood-pressure-measuring routine of FIG. 9 will be described. First, the control device 38 carries out SD1, SD2, and SD3 corresponding to the cuff-pressure changing means 60. At SD1, the control device 38 switches one or two pressure control valves 26c, 26d connected to one or two ankle cuffs 18R, 18L wound around one or two inferior limbs which has or have been judged, at SB6 or SB8 of FIG. 7, as being suspected of arteriostenosis (in particular, both the two pressure control valves 26c, 26d if at least one of the two inferior limbs has been judged, at SB8, as being suspected of arteriostenosis), to their pressure-supply positions, and operates the air pump 36, so that the pressure or pressures of the one or two ankle cuffs 18R, 18L is or are quickly increased. At SD2, the control device 38 judges whether the pressure or pressures PC of the one or two ankle cuffs 18R, 18L has or have reached the second target pressure $P_{CM}$, e.g., 240 mmHg. If a negative judgment is made at SD2, SD1 and SD2 are repeated while the cuff pressure or pressures PC is or are continuously increased.

Meanwhile, if a positive judgment is made at SD2, the control goes to SD3 to stop the air pump 36 and switch the pressure control valve or valves 26, to the slow-deflation position, so that the pressure or pressures PC of the one or two cuffs 18 is or are slowly decreased at the prescribed rate of 5 mmHg/sec.

Next, the control goes to SD4 corresponding to the ankle-blood-pressure determining means 82. More specifically described, the control device 38 determines respective amplitudes of respective heartbeat-synchronous pulses of each of the ankle pulse wave or waves WL represented by the pulse-wave signal or signals SM continuously supplied from the pulse-wave filter circuit or circuits 32, and determines a right-ankle or left-ankle systolic blood pressure $BP_{LSYS}$, a right-ankle or left-ankle diastolic blood pressure $BP_{LDIA}$, and a right-ankle or a left-ankle mean blood pressure $BP_{LMEAN}$, according to well-known oscillometric blood-pressure determining algorithm, based on the change of the determined amplitudes of the right-ankle pulse wave $WL_R$, or the change of the determined amplitudes of the left-ankle pulse wave $WL_L$.

Then, at SD5 corresponding to the cuff-pressure changing means 60, the control device 38 switches the pressure control valve or valves 26 to the quick-deflation position, so that the pressure or pressures PC of the one or two cuffs 18 is or are quickly decreased.

Then, the control goes to SD6 to operate the display device 54 to display the right-ankle or left-ankle systolic blood pressure $BP_{LSYS}$, etc. determined at SD4.

It emerges from the foregoing description of the embodiment based on the above-described flow charts, that before the ankle blood pressure $BP_L$ is measured by the ankle-blood-pressure measuring device 42, the inferior-limb pulse-wave propagation velocity baPVW, the full time period U-time, and the parameter % MAP are determined, and displayed on the display device 54, at Steps SB3, SB4, and SB5 (the stenosis-relating-pulse-wave-information obtaining means), based on the ankle pulse wave WL extracted by the pulse-wave filter circuit 32c, 32d. If that the inferior limb is not suspected of arteriostenosis can be judged based on the inferior-limb pulse-wave propagation velocity baPWV, the full time period U-time, and the parameter % MAP, it is not needed to operate the ankle-blood-pressure measuring device 42 to carry out the blood-pressure measurement to determine the index ABI. Therefore, the discomfort the patient feels when his or her inferior-limb arteriostenosis is diagnosed can be reduced.

In the embodiment based on the above-described flow charts, if it is judged at Step SB6 or SB8 that the inferior limb is suspected of arteriostenosis, the ankle-blood-pressure measuring device 42 and the upper-arm-blood-pressure measuring device 40 are automatically operated to measure the ankle blood pressure and the upper-arm blood pressure, respectively, so that the index ABI is automatically determined to an advantage.

In the embodiment based on the above-described flow charts, at Step SB2 (the normal-range determining means 70), the normal range of inferior-limb-pulse-wave propagation velocity baPWV is determined, based on the superior-limb-pulse-wave propagation velocity hbPWV, according to the relationship shown in FIG. 4 and, at SB6 (the preliminary-judgment making means 76), the preliminary judgment that the inferior limb is suspected of arteriostenosis is made if the inferior-limb-pulse-wave propagation velocity baPWV determined at SB3 (the inferior-limb-pulse-wave-propagation-velocity-relating-information obtaining means 68) does not fall in the thus determined normal range. Since the normal range is determined based on the superior-limb-pulse-wave propagation velocity hbPWV actually obtained in each measuring operation, the preliminary judgment made about whether the inferior limb is suspected of arteriostenosis is more accurate than a judgment which would be made in the case where an inferior-limb-pulse-wave propagation velocity baPWV actually measured is compared with a general-purpose normal range which is so pre-determined as to be applicable to a great number of patients.

In the embodiment based on the above-described flow charts, if at least one of the relative value $\Delta$ PWV between the left-inferior-limb-pulse-wave propagation velocity baPWV(L) and the right-inferior-limb-pulse-wave propagation velocity baPVN(R), the relative value $\Delta$ A U-time between the two full time periods U-time(L), U-time(R), and the relative value $\Delta$% MAP between the two parameter values % MAP(L), % MAP(R) is greater than a corresponding one of the respective reference values, the preliminary judgment that the inferior limb is suspected of arteriostenosis is made at SB8 (the preliminary-judgment making means 76). Thus, an accurate preliminary judgment about whether the inferior limb is suspected of arteriostenosis can be made.

While the present invention has been described in its preferred embodiment by reference to the drawings, it is to be understood that the invention may otherwise be embodied.

For example, in the illustrated embodiment, the abnormal range of inferior-limb-pulse-wave propagation velocity baPWV is determined, for each of individual patients, as the range outside the normal range determined by the normal-range determining means 70. However, the abnormal range of inferior-limb-pulse-wave propagation velocity baPWV may be a predetermined range. Contrarily, although in the illustrated embodiment the respective predetermined abnormal ranges of full time period U-time and parameter % MAP are employed, it is possible to measure a full time period U-time or a parameter % MAP from an upper arm of each of individual patients and determine, for the each individual patient, an abnormal range of full time period U-time or parameter % MAP based on the measured full time period U-time or parameter % MAP.

In the illustrated embodiment, when the preliminary-judgment making means 76 makes the judgment that the inferior limb is suspected of arteriostenosis, the ankle-blood-pressure measuring device 42 and/or the upper-arm-blood-pressure measuring device 40 are/is operated to carry out a blood-pressure measurement. However, the apparatus 10 may be modified such that when it is judged that the inferior limb is suspected of arteriostenosis, the display device 54 is operated to display characters or symbols representing the judgment. In addition, in the illustrated embodiment in which the previously-described flow charts are employed, the display device 54 is operated to display the stenosis-relating pulse-wave information (i.e., baPWV, U-time, % MAP), so that an operator can judge, from what is displayed by the display device 54, whether it is needed to measure a superior-and-inferior-limb blood-pressure index ABI of the patient. Therefore, the preliminary-judgment making means 76 may be omitted.

In addition, in the illustrated embodiment, the pulse-wave filter circuit 32 of the upper-arm-blood-pressure measuring device 40 functions as the superior-limb-pulse-wave detecting device, and the pulse-wave filter circuit 32 of the ankle-blood-pressure measuring device 42 functions as the inferior-limb-pulse-wave detecting device. However, it is possible to wear, on a superior or an inferior limb of a patient, a pulse-wave detecting device which is independent of the pulse-wave filter circuit 32 of the blood-pressure measuring device 40, 42. The pulse-wave detecting device may be a photoelectric-pulse-wave detecting probe for use in measuring blood oxygen saturation; a pressure-pulse-wave sensor which is pressed against an artery such as a radial artery via skin to detect a pressure pulse wave; an impedance-pulse-wave sensor which detects, through electrodes, an impedance of an arm or a finger; or a photoelectric-pulse-wave sensor which is worn on, e.g., an end portion of a finger to detect pulsation.

In addition, in the illustrated embodiment, the upper-arm-pulse-wave-propagation-velocity-relating information is obtained through the heart-sound microphone 44 and the upper-arm cuff 20. However, it is possible to obtain upper-arm-pulse-wave-propagation-velocity-relating information from a different combination of two portions of the patient than the combination of the heart and the upper arm. For example, since the heart is not located on a centerline of a living subject, respective distances of the two upper-arm cuffs 20 wound around the left and right upper arms 14 of the subject differ from each other. Hence, it is possible to obtain upper-arm-pulse-wave-propagation-velocity-relating information from a time difference between the respective upper-arm pulse waves $WA_R$, $WA_L$ occurring to the left and right upper-arm cuffs 20. Otherwise, it is possible to wear a photoelectric-pulse-wave sensor on an end portion of a finger to obtain upper-arm-pulse-wave-propagation-velocity-relating information from the heart (or the upper arm) and the end portion of the finger.

Moreover, in the illustrated embodiment, the inferior-limb-pulse-wave-propagation-velocity-relating information is obtained through the ankle cuff 18 and the upper-ram cuff 20. However, it is possible to obtain inferior-limb-pulse-wave-propagation-velocity-relating information from the heartsound microphone 44 and the ankle cuff 18.

It is to be understood that the present invention may be embodied with other changes, improvements and modifications that may occur to a person skilled in the art without departing from the spirit and scope of the invention defined in the appended claims.

What is claimed is:

1. An apparatus for measuring a superior-and-inferior-limb blood-pressure index of a living subject, comprising:

an inferior-limb-blood-pressure measuring device which includes at least one inferior-limb cuff adapted to be wound around at least one inferior limb of the subject and which measures at least one inferior-limb blood pressure of the inferior limb;

a superior-limb-blood-pressure measuring device which includes at least one superior-limb cuff adapted to be wound around at least one superior limb of the subject and which measures at least one superior-limb blood pressure of the superior limb;

a blood-pressure-index determining means for determining the superior-and-inferior-limb blood-pressure index, based on the inferior-limb blood pressure measured by the inferior-limb-blood-pressure measuring device and the superior-limb blood pressure measured by the superior-limb-blood-pressure measuring device;

an inferior-limb-pulse-wave detecting device which is adapted to be worn on an inferior limb of the subject and which detects an inferior-limb pulse wave from the inferior limb;

a stenosis-relating-pulse-wave-information obtaining device which obtains, based on the inferior-limb pulse wave detected by the inferior-limb-pulse-wave detecting device, stenosis-relating pulse-wave information which changes in relation with a degree of stenosis of an artery of the inferior limb;

a preliminary-judgment making means for making a preliminary judgment that the artery of the inferior limb is suspected of the stenosis, when the stenosis-relating-pulse-wave information obtained by the stenosis-relating-pulse-wave-information obtaining device falls in a predetermined abnormal range; and a blood-pressure-measurement starting means for, when the preliminary-judgment making means makes the preliminary judgment that the artery of the inferior limb is suspected of the stenosis, starting the inferior-limb-blood-pressure measuring device to measure the inferior-limb blood pressure of the inferior limb, and starting the superior-limb-blood-pressure measuring device to measure the superior-limb blood pressure of the superior limb, so that the blood-pressure-index determining means determines the superior-and-inferior-limb blood-pressure index, based on the inferior-limb blood pressure measured by the inferior-limb-blood-pressure measured by the superior-limb-blood-pressure measuring device.

2. An apparatus according to claim 1, wherein the stenosis-relating-pulse-wave-information obtaining device comprises at least one of (a) an inferior-limb-pulse-wavepropagation-velocity-relating-information obtaining device which obtains, based on the inferior-limb pulse wave detected by the inferior-limb-pulse-wave detecting device, inferior-limb-pulse-wave-propagation-velocity-relating information relating to a velocity at which the inferior-limb pulse wave propagates through the artery of the inferior limb, (b) a sharpness-degree determining means for determining a degree of sharpness of a heartbeat-synchronous pulse of the inferior-limb pulse wave detected by the inferior-limb-pulse-wave detecting device; and (c) an increase-characteristic-value determining means for determining a characteristic value of an increasing portion of a heartbeat-synchronous pulse of the inferior-limb pulse wave detected by the inferior-limb-pulse-wave detecting device.

3. An apparatus according to claim 1, wherein the stenosis-relating-pulse-wave-information obtaining device comprises an inferior-limb-pulse-wave-propagation-velocity-relating-information obtaining device which obtains, based on the inferior-limb pulse wave detected by the inferior-limb-pulse-wave detecting device, inferior-limb-pulse-wave-propagation-velocity-relating information relating to a velocity at which the inferior-limb pulse wave propagates through the artery of the inferior limb, and wherein the apparatus further comprises:

a superior-limb-pulse-wave detecting device which is adapted to be worn on a superior limb of the subject and which detects a superior-limb pulse wave from the superior limb;

a superior-limb-pulse-wave-propagation-velocity-relating-information obtaining device which obtains, based on the superior-limb pulse wave detected by the superior-limb-pulse-wave detecting device, superior-limb-pulse-wave-propagation-velocity-relating information relating to a velocity at which the superior-limb pulse wave propagates through an artery of the superior limb;

a normal-range determining means for determining, based on the superior-limb-pulse-wave-propagation-velocity-relating information obtained by the superior-limb-pulse-wave-propagation-velocity-relating-information obtaining device, a normal range of inferior-limb-pulse-wave-propagation-velocity-relating information, according to a predetermined relationship between inferior-limb-pulse-wave-propagation-velocity-relating information and superior-limb-pulse-wave-propagation-velocity-relating information; and a preliminary-judgment making means for making a preliminary judgment that the artery of the inferior limb is suspected of the stenosis, when the inferior-limb-pulse-wave-propagation-velocity-relating information obtained by the inferior-limb-pulse-wave-propagation-velocity-relating-information obtaining device does not fall in the normal range determined by the normal-range determining means.

4. An apparatus according to claim 1, wherein the inferior-limb-pulse-wave detecting device comprises two detecting members which are adapted to be worn on a left and a right inferior limb of the subject, respectively, and which detect a left-inferior-limb pulse wave and a right-inferior-limb pulse wave from the left and right inferior limbs, respectively, and wherein the stenosis-relating-pulse-wave-information obtaining device comprises means for obtaining, based on the detected left-inferior-limb pulse wave, left-limb-stenosis-relating pulse-wave information which changes in relation with a degree of stenosis of an artery of the left inferior limb, and means for obtaining, based on the detected right-inferior-limb pulse wave, right-limb-stenosis-relating pulse-wave information which changes in relation with a degree of stenosis of an artery of the right inferior limb.

5. An apparatus according to claim 4, further comprising a preliminary-judgment making means for making a preliminary judgment that the artery of at least one of the left and right inferior limbs is suspected of the stenosis, when a relative value between the obtained left-limb-stenosis-relating pulse-wave information and the obtained right-limb-stenosis-relating pulse-wave information is greater than a prescribed reference value.

6. An apparatus according to claim 1, further comprising a display device which displays at least one of the superior-and-inferior-limb blood-pressure index determined by the blood-pressure-index determining means and the stenosis-relating pulse-wave information obtained by the stenosis-relating-pulse-wave-information obtaining means.

7. An apparatus according to claim 1, wherein the blood-pressure-index determining means comprises means for determining, as the superior-and-inferior-limb blood-pressure index, at least one of a ratio of the inferior-limb blood pressure to the superior-limb blood pressure, and a ratio of the superior-limb blood pressure to the inferior-limb blood pressure.

8. An apparatus according to claim 1, wherein the inferior-limb-pulse-wave detecting device comprises a detecting member which is adapted to be worn on a first portion of the inferior limb of the patient and which detects the inferior-limb pulse wave produced by an artery of the inferior limb, and wherein the stenosis-relating-pulse-wave-information obtaining device comprises a pulse-wave sensor which is worn on a second portion of the subject that is different from the first portion of the inferior limb and which detects a heartbeat-synchronous signal from the second portion of the subject.

9. An apparatus according to claim 1, further comprising a cuff-pressure changing device which changes a pressure in each of the inferior-limb and superior-limb cuffs of the inferior-limb-blood-pressure and superior-limb-blood-pressure measuring devices.

* * * * *